(12) United States Patent
Shinozaki et al.

(10) Patent No.: US 7,943,821 B2
(45) Date of Patent: May 17, 2011

(54) STRESS-INDUCED TRANSCRIPTION FACTOR DERIVED FROM MAIZE

(75) Inventors: Kazuko Shinozaki, Tsukuba (JP); Masayuki Kakimoto, Saitama (JP); Feng Qin, Tsukuba (JP); Yoh Sakuma, Matsuyama (JP); Kyonoshin Maruyama, Tsukuba (JP)

(73) Assignee: Incorporated Administrative Agency Japan International Research Center for Agricultural Sciences, Ibaraki (JP)

( * ) Notice: Subject to any disclaimer, the term of this patent is extended or adjusted under 35 U.S.C. 154(b) by 329 days.

(21) Appl. No.: 11/991,922

(22) PCT Filed: Mar. 20, 2006

(86) PCT No.: PCT/JP2006/306057
§ 371 (c)(1),
(2), (4) Date: Mar. 11, 2008

(87) PCT Pub. No.: WO2007/032111
PCT Pub. Date: Mar. 22, 2007

(65) Prior Publication Data
US 2009/0307794 A1 Dec. 10, 2009

(30) Foreign Application Priority Data
Sep. 16, 2005 (JP) ................................. 2005-270970

(51) Int. Cl.
*C12N 15/82* (2006.01)
*C12N 15/29* (2006.01)
*A01H 5/00* (2006.01)
*C07K 14/415* (2006.01)

(52) U.S. Cl. .... 800/289; 536/23.6; 530/376; 435/320.1; 435/252.3; 800/298

(58) Field of Classification Search ........................ None
See application file for complete search history.

(56) References Cited

U.S. PATENT DOCUMENTS
7,414,172 B2 * 8/2008 Pages et al. .................. 800/295
2004/0034888 A1 2/2004 Liu et al. ...................... 800/289

FOREIGN PATENT DOCUMENTS
CA 2269105 4/2000
WO WO 00/70059 11/2000

OTHER PUBLICATIONS

M. Kakimoto et al. Functional analysis of abiotic stress responsible DREB2A-like transcription factor involved in maize, Supplement to Plant and Cell Physiology: Abstracts of Annual Meeting of the 2005, the 46th Annual Meeting of the Japanese Society of Plant Physiologists (JSPP), p. s73, Mar. 20, 2005.*
Office Action issued on August 27, 2009 in connection with corresponding Canadian Patent Application No. 2,620,766.
Liu Q., et al., "Two Transcription Factors, DREB1 and DREB2, with an EREBP/AP2 DNA Binding Domain Separate Two Cellular Signal Transduction Pathways in Drought and Low-Temperature Responsive Gene Expression, Respectively, in Arabidopsis"; The Plant Cell, vol. 10, pp. 1391-1406, (Aug. 1998).
M. Kakimoto, et al., "Functional analysis of abiotic stress responsible DREB2A-like transcription factor involved in n maize", Supplement to Plant and Cell Physiology: Abstracts of Annual Meeting of the 2005, the 46$^{th}$ Annual Meeting of the Japanese Society of Plant Physiologists (JSPP), p. s73, (Mar. 20, 2005).
Sakuma Y. et al.; "Functinal analysis of the DREB2A protein, a transcription factor that is involved in dehydration- and salt-stress response in *Arabidopsis* by using constitutive active form of DREB2A"; Abstract 1PB-047; The 26$^{th}$ Annual Meeting of the Molecular Biology Society of Japan, Kobe, Japan, Dec. 10-13, 2003.
Sakuma Y. et al.; "Analysis of transgenic *Arabidopsis* plants overexpressing a constitutive active form of DREB2A, a transcription factor that is involved in dehydration- and salt-stress response"; Abstract 1PB-515; The 27$^{th}$ Annual Meeting of the Molecular Biology Society of Japan, Kobe, Japan, Dec. 8-11, 2004.

* cited by examiner

*Primary Examiner* — Cynthia Collins
(74) *Attorney, Agent, or Firm* — Davidson, Davidson & Kappel, LLC

(57) ABSTRACT

This invention relates to a stress-inducible transcription factor derived from maize, a gene encoding the same, and a method for using the same. Specifically, this invention provides a gene comprising the following DNA (a) or (b): (a) DNA consisting of the nucleotide sequence as shown in SEQ ID NO: 1; or (b) maize-derived DNA hybridizing under stringent conditions with DNA consisting of a nucleotide sequence that is complementary to the DNA consisting of the nucleotide sequence as shown in SEQ ID NO: 1 and encoding a protein that regulates the transcription of a gene located downstream of a stress responsive element. Further, this invention relates to a transgenic plant having improved tolerance to environmental stress, such as high-temperature or dehydration stress, into which such gene has been introduced.

11 Claims, 16 Drawing Sheets

Fig. 1A

```
   1  GGGGGGGGGCTCCACGTCCACGGTATCCATAAGCTTGATGGTCTTATCCACTCCAACAACA   60
  61  ACACACTACACACCGCCACGCACATACCCAAGCCCTACGAAGCCAGTCCCCATCTTTCCA  120
 121  GCCCCCATGACCCTCGATCACAACCATCCCATCCCGATCCACCCCCCCCCCCCTCCACCCC  180
 181  CCAACACCATATCCACCACACCCAGTCCTGTCGTCCATCGTTCCATCACAACACTACCA   240
 241  AGAACCGACCTCCCACATCACCACATCCCCCTACGTCAGTCCCACCTGTCATCCACCCGT  300
 301  CCCCTCACCCCAACAACCATTTCCAGTATCACCAATCTGACCACCCAAACCCACCAACAA  360
 361  AACCACCTCCAAACCGTTCCAAGAACCCCTGTATCAACCCAAAACCCCCCCCTCACAATA  420
 421  CTCAATGTCCATACCCGTCCACGTCACCCACCGTACTTCCCCGAAGTCCGTTCCTCAAATAA  480
 481  GACACCCAAATCGTGTCCACAGACTCTCCCTCCGTACCTTCCCAACCCCCACCATCCAG   540
 541  CTACCCCCTATCACCACCCACCCAGACCCATGTATCCAGACTTCCCACCCACTAACTTCC  600
 601  CCCGACACCATCCAACAACCTCTCCCCAACCTCCTCTAGCATCGACCTCTCCCACCCTG   660
 661  CTCCAACACCTGTCCAACCTCTTCACACTCCCACGTCATCCCAGTCCACAACCACATCAA  720
 721  ATTACTCCCACATCCCATCCACCTCACACAACCCTGAACCCCTCTGACATCTCCACCCTCCC  780
 781  TAAACCCAAAATCCCCACCTCCATCATGTCCGTATCCAAGACCCGTACACCCAGTGTACCTG  840
 841  ACAACGACGTCTTTCCCCCCGTTCCACCCTATCACAAATCTTCCACATCGTCGTGATCGTT  900
 901  TTCATATCCGTGACATCCTCACCATCATCCAAACCCATCCACATAATCCACGTCCACCTG  960
 961  ACCCTCCCATCCCCCACCCCTCGTGTCTTCATCACCCTCCATTCCAGTGTCTTCCACACCA 1020
1021  TCCTCCACCCACACCCACACCCACACCCATTCCTCATGTCTCAACAACCCCACATGTTTC 1080
1081  TTCCTCCCTTCCAAACCCCTCGTTTCGTCCACCCGTCTCCACCCCCTAAACTGAATTTCTG 1140
1141  ATGTTTCACCCGTTCATCCTCATCCCACTTCATGTCTCACCTTGTCAATTCCCACCCAAAC 1200
1201  ATTCCCACAACTTATAACCTCTACCAATTCTACCCCTTTTATATTCCTCTGTAAATACTTC 1260
```
(SEQ ID NO:5)

Fig. 1B

```
   1  CCCCTCCCCCCGTCCCCCCCCTCTACAACTAGTCCATCCCCCCCCCTCCNCCAATTCCA   60
  61  TCGTCTTATCCGACTCCAACAACAACACACTACACACCACCCACCCACATACCCAACCCTA  120
 121  CCAACCCAGTCCCCATCTTTCCAGCCCCATCACCCCTCCATCACAACCATCCCATCCCGA  180
                                        M  T  L  D  Q  N  H  A  M  P
 181  TCCAGCCCCCCCCCTCCAGCCCCCGAACGACAACCGACCTCCCAGATCACCACATCCCC  240
        M  Q  P  P  A  L  Q  P  G  R  K  K  R  P  R  R  S  R  D  G
 241  CTACGTCAGTCCCCACCTGTCATCCAACGTCCCCTGACCCCAACAACCATTTCCAGTATG  300
        P  T  S  V  A  A  V  I  Q  R  W  A  E  R  N  K  H  L  E  Y
 301  ACCAATCTCACCACCCAAACCGACCAACAAAACCACCTCCAAACCGTTCCAACAACCCCT  360
        E  E  S  E  E  A  K  R  P  R  K  A  P  A  K  G  S  K  K  G
 361  GTATGAACCCAAAACCCCCCCCTGACAATACTCAATGTCCATACCCGTCCAGTCACCCACC  420
        C  M  K  G  K  G  G  P  D  N  T  Q  C  G  Y  R  G  V  R  Q
 421  GTACTTCCCCCAAGTCCCGTTCCTCAAATAACAGACCCAAATCGTCGTCCACAGACTCTCCC  480
        R  T  W  G  K  W  V  A  E  I  R  E  P  N  R  V  D  R  L  W
 481  TCCGTACCTTCCAACCCCCCGACCATCCACTACCCCCTATGACCACCACCAGACCTA  540
        L  G  T  F  P  T  A  E  D  A  A  R  A  Y  D  E  A  A  R  A
 541  TGTATCCAGACTTCCCACCCACTAACTTCCCCCCACACCATCCAACAACCTCTCCCCAAG  600
        M  Y  G  D  L  A  R  T  N  F  P  G  Q  D  A  T  T  S  A  Q
 601  CTCCTCTACCATCCACCCTCTCCCCACCCTCCTCCAACACCTGTCCAACCTCTTCAGACTG  660
        A  A  L  A  S  T  S  A  Q  A  A  P  T  A  V  E  A  L  Q  T
 661  CCACGTCATCCCAGTCCACAACCACATCAAATTACTCCGACATCCCATCCACCTCACACA  720
        G  T  S  C  E  S  T  T  T  S  N  Y  S  D  I  A  S  T  S  H
 721  ACCCTGAACCCTCTCGACATCTCCACCTCCCTAAACCCAAAATCCCCACCTCCATCATGTG  780
        K  P  E  A  S  D  I  S  S  S  L  K  A  K  C  P  A  G  S  C
 781  GTATCCAACACCGTACACCCAGTGTACCTCACAACCACGTCTTTCCCCCCGTTCCACCCTA  840
        G  I  Q  E  G  T  P  S  V  A  D  K  E  V  F  G  P  L  E  P
 841  TCACAAATCTTCCACATCGTCGTCATCGTTTTCATATCCCGTCACATCCTCACCATCATCG  900
        I  T  N  L  P  D  G  G  D  G  F  D  I  G  E  M  L  R  M  M
 901  AAACCCCATCCACATAATCCACGTCCACCTCACCCTCCCATCCCCCACCCCTCGTGTCTTG  960
        E  S  D  P  H  N  A  G  G  A  D  A  G  M  G  Q  P  W  C  L
 961  ATGACCCTCCATTCCAGTGTCTTCCAGACCCATCCTCCAGCCCACACCCAGACCCAGACCCAT 1020
        D  E  L  D  S  S  V  L  E  S  M  L  Q  P  Q  P  E  P  E  P
1021  TCCTCATGTCTCAACAACCCCACATGTTCTTCCTCCCCTTCCAAACCCCTCCGTTTCGTCG 1080
        F  L  M  S  E  E  P  D  M  F  L  A  G  F  E  S  A  G  F  V
1081  ACCCGTCTCCACCCCCTAAACTGAATTTCTCATGTTTGACCCGTTGATCCTCATCCCACTTC 1140
        E  G  L  E  R  L  N  *  (SEQ ID NO:2)
1141  ATGTCTCACCTTGTCAATTCCCACCCAAACATTCCCACAACTTATAACCTCTACCAATTC 1200
1201  TACCCCTTTTATATTCCCTCTGTAAATAGTTCTCTAGTCATCCCAACTCCCGTTTCCTTCACA 1260
1261  TTTTTTGTAACACCACAACGTCATGCAAATAGTTCCCACCCTTGTCCAACCACAACAAAAAA 1320
1321  ATAAATAAAACGACTGCCTTCCTTTATCAACCTTATCCATACCCGTCCACCCTCCAGCCCCC 1380
1381  CC (SEQ ID NO:6)                                              1382
```

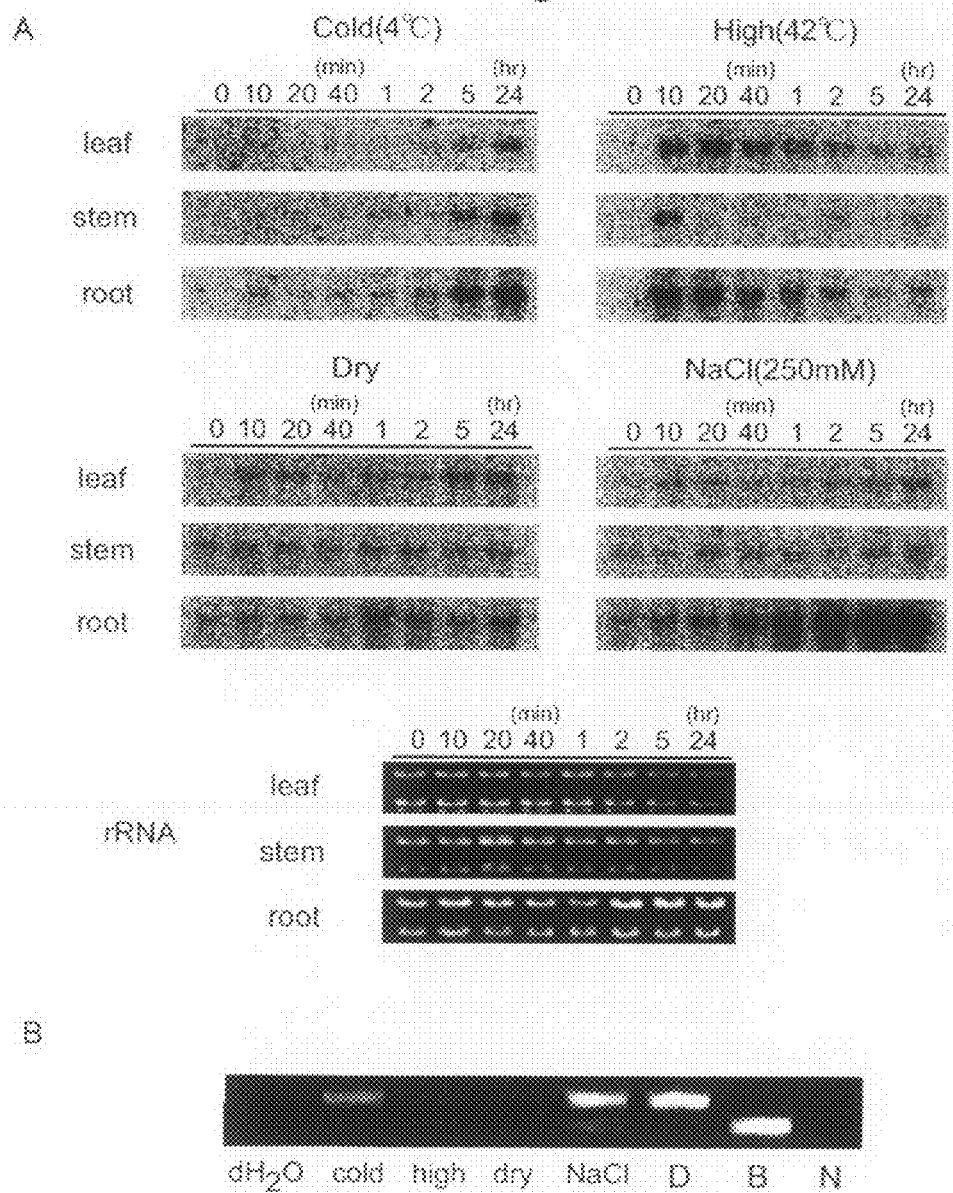

Fig. 3
A
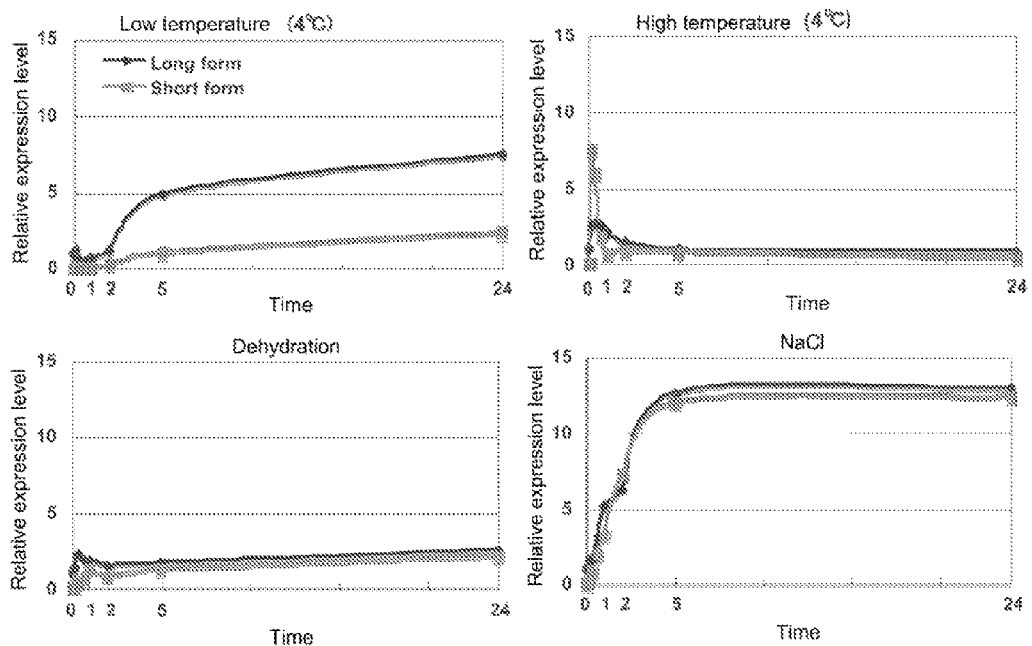
B
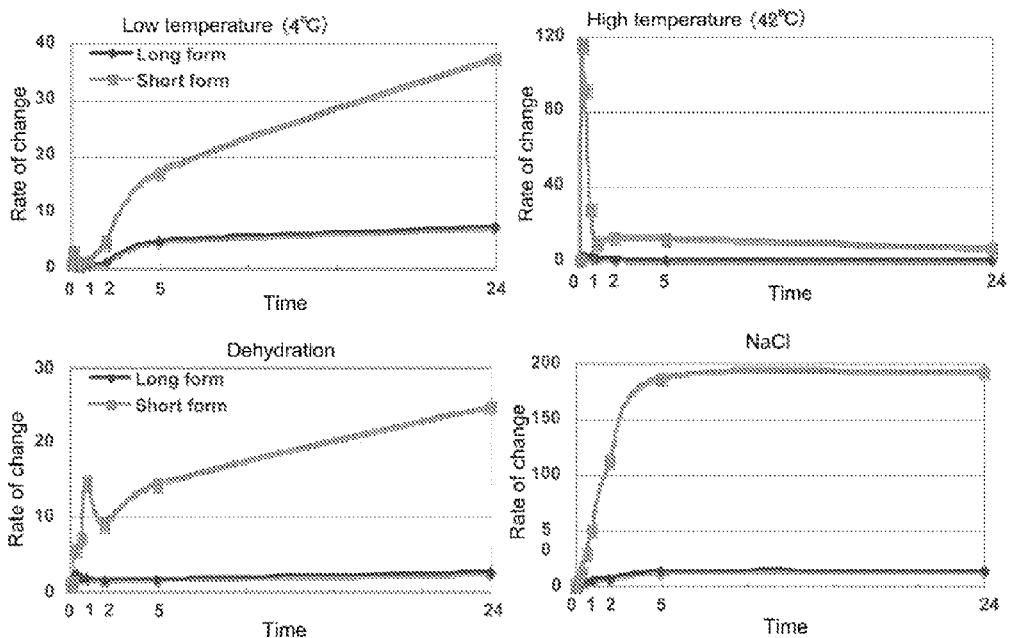

Fig. 6

```
ZmDREB2A  224: VFGPLEPI TNLPDOG-DG-FD GEMLRMMESDP 254 (SEQ ID NO:7)
HvDRF1    288: VYEPLEPI SNLPDOEAD-OFD EELLKLMEADP 319 (SEQ ID NO:8)
OsDREB2B  303: VFEPLEPI ASLPEDOODYOFD DEMLRMMEADP 335 (SEQ ID NO:9)
PgDREB2A  238: VFEPLEPI ENLPEODFDG-FD DEMLRMMEADP 269 (SEQ ID NO:10)
               *  *****  **   *  ***  *  **  **
```

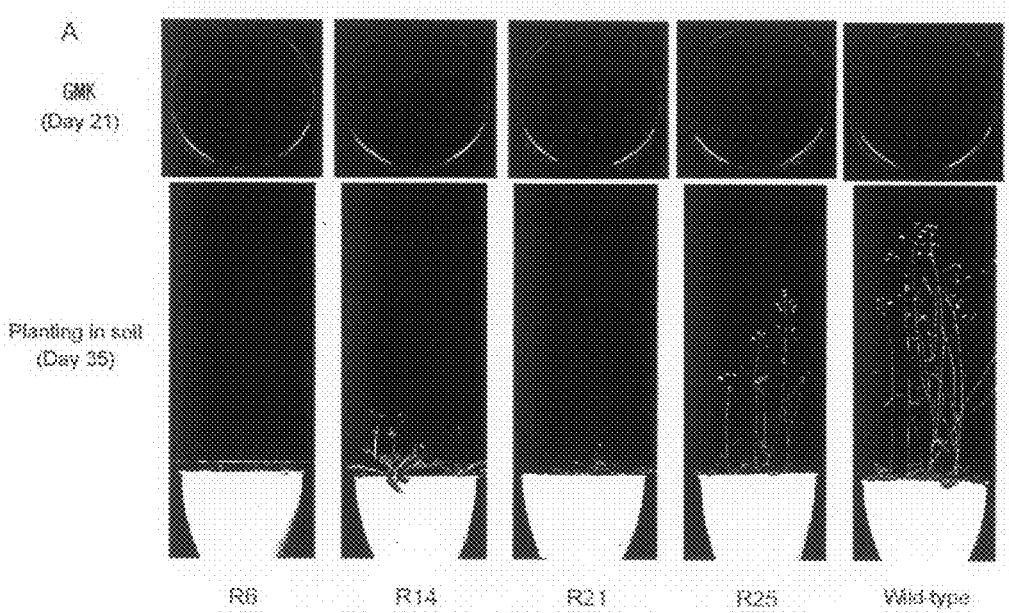
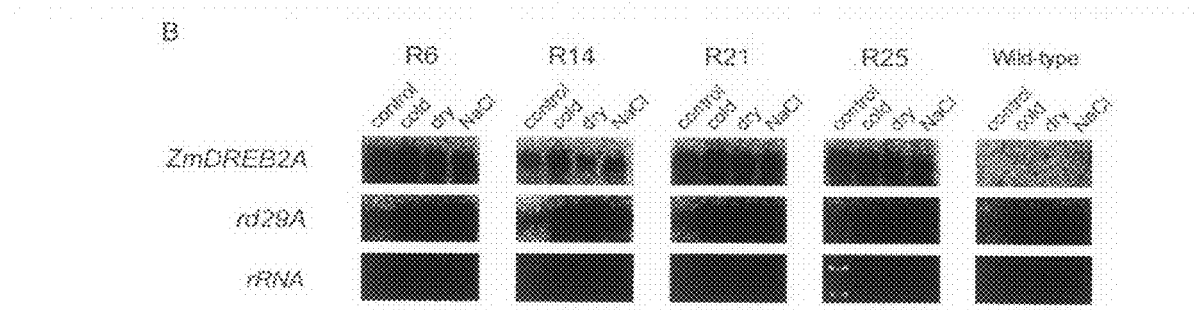
Fig. 8

Fig. 10
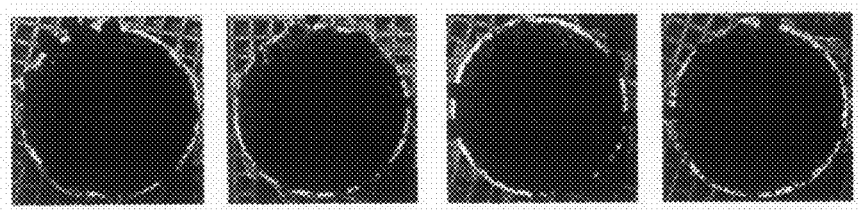
Control
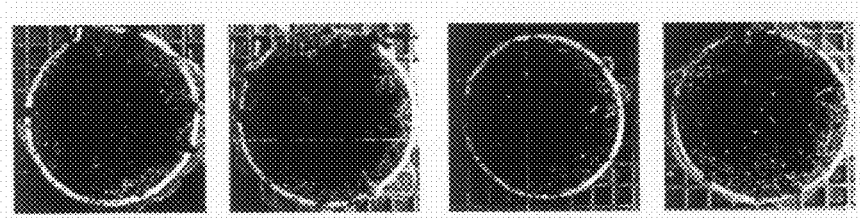
4 days after
heat shock
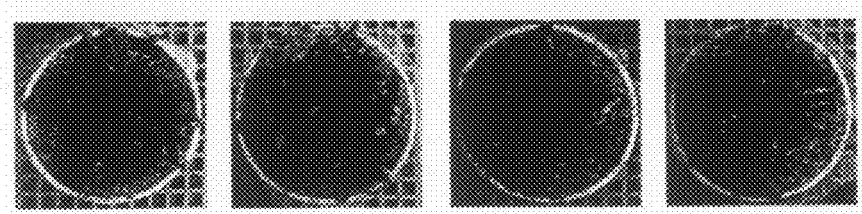
7 days after
heat shock
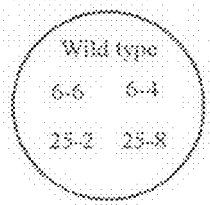

| Treating temperature | Control | | | DREB2A CA OX | | |
|---|---|---|---|---|---|---|
| | Number of surviving individuals | Number of total individuals | % | Number of surviving individuals | Number of total individuals | % |
| 22° C | 78 | 78 | 100.0 | 65 | 73 | 89.0 |
| 42° C | 73 | 75 | 97.3 | 75 | 76 | 98.7 |
| 43° C | 53 | 53 | 100.0 | 74 | 74 | 100.0 |
| 44° C | 38 | 50 | 76.0 | 75 | 75 | 100.0 |
| 45° C | 1 | 50 | 2.0 | 74 | 75 | 98.7 |

```
                       SEQUENCE LISTING

<160> NUMBER OF SEQ ID NOS: 10

<210> SEQ ID NO 1
<211> LENGTH: 1283
<212> TYPE: DNA
<213> ORGANISM: Zea mays L
<220> FEATURE:
<223> OTHER INFORMATION: ZmDREB2A cDNA (Short form)
<220> FEATURE:
<221> NAME/KEY: CDS
<222> LOCATION: (89)..(1042)

<400> SEQUENCE: 1
ggtcttatcg actccaacaa gaacacacta cacaccagcc agcgagatag cgaacgctag        60
gaacccagtg gccatctttg gagcggcc atg acg ctg gat cag aac cat gcc           112
                                Met Thr Leu Asp Gln Asn His Ala
                                  1               5 atg ccg atg cag ccc ccg gcc ctg cag ccc gga agg aag aag cga cct          160
Met Pro Met Gln Pro Pro Ala Leu Gln Pro Gly Arg Lys Lys Arg Pro
     10                  15                  20 cgc aga tca cga gat ggg cct acg tca gtg gca gct gtc atc cag cgg          208
Arg Arg Ser Arg Asp Gly Pro Thr Ser Val Ala Ala Val Ile Gln Arg
 25                  30                  35                  40 tgg gct gag cgc aac aag cat ttg gag tat gag gaa tct gag gag gca          256
Trp Ala Glu Arg Asn Lys His Leu Glu Tyr Glu Glu Ser Glu Glu Ala
                 45                  50                  55 aag cga cca aga aaa gca cct gca aag ggt tcg aag aag ggc tgt atg          304
Lys Arg Pro Arg Lys Ala Pro Ala Lys Gly Ser Lys Lys Gly Cys Met
             60                  65                  70
```

```
aag gga aaa ggg ggg cct gac aat act caa tgt gga tac cgt gga gtg       352
Lys Gly Lys Gly Gly Pro Asp Asn Thr Gln Cys Gly Tyr Arg Gly Val
            75                  80                  85 agg cag cgt act tgg ggg aag tgg gtt gct gaa ata aga gag cca aat       400
Arg Gln Arg Thr Trp Gly Lys Trp Val Ala Glu Ile Arg Glu Pro Asn
    90                  95                 100 cgt gtc gac aga ctc tgg ctg ggt acc ttc cca acc gcg gag gat gca       448
Arg Val Asp Arg Leu Trp Leu Gly Thr Phe Pro Thr Ala Glu Asp Ala
105                 110                 115                 120 gct agg gcc tat gac gag gca gcc aga gcg atg tat gga gac ttg gca       496
Ala Arg Ala Tyr Asp Glu Ala Ala Arg Ala Met Tyr Gly Asp Leu Ala
                125                 130                 135 cgg act aac ttc ccc gga cag gat gca aca acc tct gcc caa gct gct       544
Arg Thr Asn Phe Pro Gly Gln Asp Ala Thr Thr Ser Ala Gln Ala Ala
            140                 145                 150 cta gca tcg acc tct gcc cag gct gct cca aca gct gtc gaa gct ctt       592
Leu Ala Ser Thr Ser Ala Gln Ala Ala Pro Thr Ala Val Glu Ala Leu
        155                 160                 165 cag act ggc acg tca tgc gag tcg aca acg aca tca aat tac tcg gac       640
Gln Thr Gly Thr Ser Cys Glu Ser Thr Thr Thr Ser Asn Tyr Ser Asp
    170                 175                 180 atc gca tcc acc tca cac aag cct gaa gcc tct gac atc tcg agc tcc       688
Ile Ala Ser Thr Ser His Lys Pro Glu Ala Ser Asp Ile Ser Ser Ser
185                 190                 195                 200 cta aag gca aaa tgc cca gct gga tca tgt ggt atc caa gag ggt aca       736
Leu Lys Ala Lys Cys Pro Ala Gly Ser Cys Gly Ile Gln Glu Gly Thr
                205                 210                 215 ccc agt gta gct gac aag gag gtc ttt ggg ccg ttg gag cct atc aca       784
Pro Ser Val Ala Asp Lys Glu Val Phe Gly Pro Leu Glu Pro Ile Thr
            220                 225                 230 aat ctt cca gat ggt ggt gat ggt ttt gat atc ggt gag atg ctg agg       832
Asn Leu Pro Asp Gly Gly Asp Gly Phe Asp Ile Gly Glu Met Leu Arg
        235                 240                 245 atg atg gaa agc gat cca cat aat gca ggt gga gct gac gct ggc atg       880
Met Met Glu Ser Asp Pro His Asn Ala Gly Gly Ala Asp Ala Gly Met
    250                 255                 260 ggg cag ccc tgg tgt ctt gat gag ctg gat tcg agt gtc ttg gag agc       928
Gly Gln Pro Trp Cys Leu Asp Glu Leu Asp Ser Ser Val Leu Glu Ser
265                 270                 275                 280 atg ctc cag cca cag cca gag cca gag cca ttc ctg atg tct gaa gaa       976
Met Leu Gln Pro Gln Pro Glu Pro Glu Pro Phe Leu Met Ser Glu Glu
                285                 290                 295 ccg gac atg ttt ctt gct ggc ttc gaa agc gct ggt ttc gtc gag ggt      1024
Pro Asp Met Phe Leu Ala Gly Phe Glu Ser Ala Gly Phe Val Glu Gly
            300                 305                 310 ctg gag cgg cta aac tga atttctgatg tttgaccgtt gatcctcatc             1072
Leu Glu Arg Leu Asn
            315 ccacttcatg tctgagcttg tgaattcgga ggcaaacatt ggcagaactt ataagctcta    1132 gcaattctag gcttttatat tcctctgtaa atagttctct agtcatggga actgggtttg    1192 cttcacattt tttgtaagac cagaagtgat gtaaatagtt cccacccttgt ggaaggacaa   1252 gaaaaaaata aataaaaaga gtgcttgctt t                                   1283

<210> SEQ ID NO 2
<211> LENGTH: 317
<212> TYPE: PRT
<213> ORGANISM: Zea mays L
<220> FEATURE:
<223> OTHER INFORMATION: ZmDREB2A cDNA (Short form)
```

-continued

<400> SEQUENCE: 2

```
Met Thr Leu Asp Gln Asn His Ala Met Pro Met Gln Pro Pro Ala Leu
 1               5                  10                  15

Gln Pro Gly Arg Lys Lys Arg Pro Arg Arg Ser Arg Asp Gly Pro Thr
                20                  25                  30

Ser Val Ala Ala Val Ile Gln Arg Trp Ala Glu Arg Asn Lys His Leu
            35                  40                  45

Glu Tyr Glu Glu Ser Glu Glu Ala Lys Arg Pro Arg Lys Ala Pro Ala
 50                  55                  60

Lys Gly Ser Lys Lys Gly Cys Met Lys Gly Lys Gly Pro Asp Asn
 65                  70                  75                  80

Thr Gln Cys Gly Tyr Arg Gly Val Arg Gln Arg Thr Trp Gly Lys Trp
                85                  90                  95

Val Ala Glu Ile Arg Glu Pro Asn Arg Val Asp Arg Leu Trp Leu Gly
            100                 105                 110

Thr Phe Pro Thr Ala Glu Asp Ala Ala Arg Ala Tyr Asp Glu Ala Ala
        115                 120                 125

Arg Ala Met Tyr Gly Asp Leu Ala Arg Thr Asn Phe Pro Gly Gln Asp
130                 135                 140

Ala Thr Thr Ser Ala Gln Ala Ala Leu Ala Ser Thr Ser Ala Gln Ala
145                 150                 155                 160

Ala Pro Thr Ala Val Glu Ala Leu Gln Thr Gly Thr Ser Cys Glu Ser
                165                 170                 175

Thr Thr Thr Ser Asn Tyr Ser Asp Ile Ala Ser Thr Ser His Lys Pro
            180                 185                 190

Glu Ala Ser Asp Ile Ser Ser Leu Lys Ala Lys Cys Pro Ala Gly
        195                 200                 205

Ser Cys Gly Ile Gln Glu Gly Thr Pro Ser Val Ala Asp Lys Glu Val
210                 215                 220

Phe Gly Pro Leu Glu Pro Ile Thr Asn Leu Pro Asp Gly Gly Asp Gly
225                 230                 235                 240

Phe Asp Ile Gly Glu Met Leu Arg Met Met Glu Ser Asp Pro His Asn
                245                 250                 255

Ala Gly Gly Ala Asp Ala Gly Met Gly Gln Pro Trp Cys Leu Asp Glu
            260                 265                 270

Leu Asp Ser Ser Val Leu Glu Ser Met Leu Gln Pro Gln Pro Glu Pro
        275                 280                 285

Glu Pro Phe Leu Met Ser Glu Glu Pro Asp Met Phe Leu Ala Gly Phe
    290                 295                 300

Glu Ser Ala Gly Phe Val Glu Gly Leu Glu Arg Leu Asn
305                 310                 315
```

<210> SEQ ID NO 3
<211> LENGTH: 1336
<212> TYPE: DNA
<213> ORGANISM: Zea mays L
<220> FEATURE:
<223> OTHER INFORMATION: ZmDREB2A cDNA (Long form)
<220> FEATURE:
<221> NAME/KEY: CDS
<222> LOCATION: (89)..(358)

<400> SEQUENCE: 3

```
ggtcttatcg actccaacaa gaacacacta cacaccagcc agcgagatag cgaacgctag      60
gaacccagtg gccatctttg gagcggcc atg acg ctg gat cag aac cat gcc        112
                                Met Thr Leu Asp Gln Asn His Ala
                                 1               5
```

```
atg ccg atg cag ccc ccg gcc ctg cag ccc gga aga gca tat gga gca      160
Met Pro Met Gln Pro Pro Ala Leu Gln Pro Gly Arg Ala Tyr Gly Ala
     10              15                  20 gag ggc agt gct gtg gtg cat ggt tcc atc aga aca gta gga aga agc      208
Glu Gly Ser Ala Val Val His Gly Ser Ile Arg Thr Val Gly Arg Ser
 25              30                  35                  40 gac ctc gca gat cac gag atg ggc cta cgt cag tgg cag ctg tca tcc      256
Asp Leu Ala Asp His Glu Met Gly Leu Arg Gln Trp Gln Leu Ser Ser
                 45                  50                  55 agc ggt ggg ctg agc gca aca agc att tgg agt atg agg aat ctg agg      304
Ser Gly Gly Leu Ser Ala Thr Ser Ile Trp Ser Met Arg Asn Leu Arg
             60                  65                  70 agg caa agc gac caa gaa aag cac ctg caa agg gtt cga aga agg gct      352
Arg Gln Ser Asp Gln Glu Lys His Leu Gln Arg Val Arg Arg Arg Ala
         75                  80                  85 gta tga agggaaaagg ggggcctgac aatactcaat gtggataccg tggagtgagg        408
Val
     90 cagcgtactt gggggaagtg ggttgctgaa ataagagagc caaatcgtgt cgacagactc    468
tggctgggta ccttcccaac cgcggaggat gcagctaggg cctatgacga ggcagccaga    528
gcgatgtatg gagacttggc acggactaac ttccccggac aggatgcaac aacctctgcc    588
caagctgctc tagcatcgac ctctgcccag gctgctccaa cagctgtcga agctcttcag    648
actggcacgt catgcgagtc gacaacgaca tcaaattact cggacatcgc atccacctca    708
cacaagcctg aagcctctga catctcgagc tccctaaagg caaaatgccc agctggatca    768
tgtggtatcc aagagggtac acccagtgta gctgacaagg aggtctttgg gccgttggag    828
cctatcacaa atcttccaga tggtggtgat ggttttgata tcggtgagat gctgaggatg    888
atggaaagcg atccacataa tgcaggtgga gctgacgctg gcatgggggca gccctggtgt    948
cttgatgagc tggattcgag tgtcttggag agcatgctcc agccacagcc agagccagag   1008
ccattcctga tgtctgaaga accggacatg tttcttgctg gcttcgaaag cgctggtttc   1068
gtcgagggtc tggagcggct aaactgaatt tctgatgttt gaccgttgat cctcatccca   1128
cttcatgtct gagcttgtga attcggaggc aaacattggc agaacttata agctctagca   1188
attctaggct tttatattcc tctgtaaata gttctctagt catgggaact gggtttgctt   1248
cacatttttt gtaagaccag aagtgatgta aatagttccc accttgtgga aggacaagaa   1308
aaaaataaat aaaagagtg cttgctttt                                       1336

<210> SEQ ID NO 4
<211> LENGTH: 89
<212> TYPE: PRT
<213> ORGANISM: Zea mays L
<220> FEATURE:
<223> OTHER INFORMATION: ZmDREB2A cDNA (Long form)

<400> SEQUENCE: 4

Met Thr Leu Asp Gln Asn His Ala Met Pro Met Gln Pro Pro Ala Leu
 1               5                  10                  15

Gln Pro Gly Arg Ala Tyr Gly Ala Glu Gly Ser Ala Val Val His Gly
             20                  25                  30

Ser Ile Arg Thr Val Gly Arg Ser Asp Leu Ala Asp His Glu Met Gly
         35                  40                  45

Leu Arg Gln Trp Gln Leu Ser Ser Ser Gly Gly Leu Ser Ala Thr Ser
     50                  55                  60

Ile Trp Ser Met Arg Asn Leu Arg Arg Gln Ser Asp Gln Glu Lys His
```

```
                65                  70                  75                  80
Leu Gln Arg Val Arg Arg Arg Ala Val
                    85

<210> SEQ ID NO 5
<211> LENGTH: 1260
<212> TYPE: DNA
<213> ORGANISM: Zea mays

<400> SEQUENCE: 5 gggccccct cgaggtcgac ggtatcgata agcttgatgg tcttatcgac tccaacaaga      60
acacactaca caccagccag cgagatagcg aacgctagga acccagtggc catctttgga     120
gcggccatga cgctggatca gaaccatgcc atgccgatgc agccccggcc cctgcagccc     180
ggaagagcat atggagcaga gggcagtgct gtggtgcatg gttccatcag aacagtagga     240
agaagcgacc tcgcagatca cgagatgggc ctacgtcagt ggcagctgtc atccagcggt     300
gggctgagcg caacaagcat ttggagtatg aggaatctga ggaggcaaag cgaccaagaa     360
aagcacctgc aaagggttcg aagaagggct gtatgaaggg aaaaggggggg cctgacaata    420 ctcaatgtgg ataccgtgga gtgaggcagc gtacttgggg gaagtgggtt gctgaaataa     480
gagagccaaa tcgtgtcgac agactctggc tgggtacctt cccaaccgcg gaggatgcag     540
ctagggccta tgacgaggca gccagagcga tgtatgagga cttggcacgg actaacttcc     600
ccggacagga tgcaacaacc tctgcccaag ctgctctagc atcgacctct gcccaggctg     660
ctccaacagc tgtcgaagct cttcagactg gcacgtcatg cgagtcgaca acgacatcaa     720
attactcgga catcgcatcc acctcacaca agcctgaagc ctctgacatc tcgagctccc     780
taaaggcaaa atgcccagct ggatcatgtg gtatccaaga gggtacaccc agtgtagctg     840
acaaggaggt ctttgggccg ttggagccta tcacaaatct tccagatggt ggtgatggtt     900
ttgatatcgg tgagatgctg aggatgatgg aaagcgatcc acataatgca ggtggagctg     960
acgctggcat ggggcagccc tggtgtcttg atgagctgga ttcgagtgtc ttggagagca    1020
tgctccagcc acagccagag ccagagccat tcctgatgtc tgaagaaccg acatgtttc     1080 ttgctggctt cgaaagcgct ggtttcgtcg agggtctgga gcggctaaac tgaatttctg    1140
atgtttgacc gttgatcctc atcccacttc atgtctgagc ttgtgaattc ggaggcaaac    1200
attggcagaa cttataagct ctagcaattc taggctttta tattcctctg taaatagttc    1260

<210> SEQ ID NO 6
<211> LENGTH: 1382
<212> TYPE: DNA
<213> ORGANISM: Zea mays
<220> FEATURE:
<221> NAME/KEY: misc_feature
<222> LOCATION: (51)..(51)
<223> OTHER INFORMATION: n is a, c, g, or t

<400> SEQUENCE: 6
gggctcccgc ggtggcggcc gctctagaac tagtggatcc cccgggctgc nggaattcga     60
tggtcttatc gactccaaca agaacacact acacaccagc cagcgagata gcgaacgcta    120
ggaacccagt ggccatcttt ggagcggcca tgacgctgga tcagaaccat gccatgccga    180
tgcagccccc ggccctgcag cccggaagga agaagcgacc tcgcagatca cgagatgggc    240
ctacgtcagt ggcagctgtc atccagcggt gggctgagcg caacaagcat ttggagtatg    300
aggaatctga ggaggcaaag cgaccaagaa aagcacctgc aaagggttcg aagaagggct    360
gtatgaaggg aaaaggggggg cctgacaata ctcaatgtgg ataccgtgga gtgaggcagc    420
```

```
gtacttgggg gaagtgggtt gctgaaataa gagagccaaa tcgtgtcgac agactctggc      480
tgggtacctt cccaaccgcg gaggatgcag ctagggccta tgacgaggca gccagagcga      540
tgtatggaga cttggcacgg actaacttcc ccggacagga tgcaacaacc tctgcccaag      600
ctgctctagc atcgacctct gcccaggctg ctccaacagc tgtcgaagct cttcagactg      660
gcacgtcatg cgagtcgaca acgacatcaa attactcgga catcgcatcc acctcacaca      720
agcctgaagc ctctgacatc tcgagctccc taaaggcaaa atgcccagct ggatcatgtg      780
gtatccaaga gggtacaccc agtgtagctg caaggaggt cttttgggccg ttggagccta      840 tcacaaatct tccagatggt ggtgatggtt ttgatatcgg tgagatgctg aggatgatgg      900
aaagcgatcc acataatgca ggtggagctg acgctggcat ggggcagccc tggtgtcttg      960
atgagctgga ttcgagtgtc ttggagagca tgctccagcc acagccagag ccagagccat     1020
tcctgatgtc tgaagaaccg gacatgtttc ttgctggctt cgaaagcgct ggtttcgtcg     1080
agggtctgga gcggctaaac tgaatttctg atgtttgacc gttgatcctc atcccacttc     1140
atgtctgagc ttgtgaattc ggaggcaaac attggcagaa cttataagct ctagcaattc     1200 taggcttta tattcctctg taaatagttc tctagtcatg ggaactgggt ttgcttcaca     1260 tttttgtaa gaccagaagt gatgtaaata gttcccacct tgtggaagga caagaaaaaa     1320
ataaataaaa agagtgcttg ctttatcaag cttatcgata ccgtcgacct cgagggggggc     1380 cc                                                                    1382

<210> SEQ ID NO 7
<211> LENGTH: 31
<212> TYPE: PRT
<213> ORGANISM: Zea mays

<400> SEQUENCE: 7

Val Phe Gly Pro Leu Glu Pro Ile Thr Asn Leu Pro Asp Gly Gly Asp
  1               5                  10                  15

Gly Phe Asp Ile Gly Glu Met Leu Arg Met Met Glu Ser Asp Pro
             20                  25                  30

<210> SEQ ID NO 8
<211> LENGTH: 32
<212> TYPE: PRT
<213> ORGANISM: Hordeum vulgare

<400> SEQUENCE: 8

Val Tyr Glu Pro Leu Glu Pro Ile Ser Asn Leu Pro Asp Gly Glu Ala
  1               5                  10                  15

Asp Cys Phe Asp Ile Glu Glu Leu Leu Lys Leu Met Glu Ala Asp Pro
             20                  25                  30

<210> SEQ ID NO 9
<211> LENGTH: 33
<212> TYPE: PRT
<213> ORGANISM: Oryza sativa

<400> SEQUENCE: 9

Val Phe Glu Pro Leu Glu Pro Ile Ala Ser Leu Pro Glu Asp Gln Gly
  1               5                  10                  15

Asp Tyr Cys Phe Asp Ile Asp Glu Met Leu Arg Met Met Glu Ala Asp
             20                  25                  30

Pro
```

```
-continued

<210> SEQ ID NO 10
<211> LENGTH: 32
<212> TYPE: PRT
<213> ORGANISM: Pennisetum glaucum

<400> SEQUENCE: 10

Val Phe Glu Pro Leu Glu Pro Ile Glu Asn Leu Pro Glu Gly Asp Phe
 1               5                  10                  15

Asp Gly Phe Asp Ile Asp Glu Met Leu Arg Met Met Glu Ala Asp Pro
            20                  25                  30
```

US 7,943,821 B2

STRESS-INDUCED TRANSCRIPTION FACTOR DERIVED FROM MAIZE

This application is a national phase of International Application No. PCT/JP2006/306057, filed Mar. 20, 2006, which claims priority to Japanese Application No. 2005-270970, filed Sep. 16, 2005.

TECHNICAL FIELD

The present invention relates to a stress-inducible transcription factor derived from maize, a gene encoding the same, and a method for using the same.

BACKGROUND ART

Plants possess tolerance mechanisms to cope with various types of environmental stresses in nature such as dehydration, high-temperature, freezing, or salt stress. Genes that respond to such various types of environmental stresses are considered to overlap, and tolerance to each stress is considered to be attained as a result of closely-related intracellular responses (Plant Physiol., 115: 327-334, 1997). However, genes that respond to each stress are different among temperature, dehydration, and salt stresses, and it is suggested that such genes have systems for separately recognizing each stress.

In the past, the present inventors have isolated and identified transcription factors that bind to a stress responsive cis-element, specifically activate the transcription of genes located downstream thereof, and impart environmental stress tolerance to plants. Examples include the DREB genes, such as DREB1A, DREB1B, DREB1C, DREB2A, and DREB2B genes, from *Arabidopsis thaliana* (Japanese Patent Publication (kokai) No. 10-228457 A (1998)). They reported that introduction and overexpression of the genes in a plant enabled stress tolerance to be imparted without the retardation of a plant (Japanese Patent Publication (kokai) 10-292348 A (1998)).

DREB proteins are roughly classified into the DREB1 type and the DREB2 type, and both of them have DNA-binding domains (AP2/ERF domains) that recognize and bind to the DRE sequence. DREB1 orthologs of DREB genes in various plants such as rice and maize have been studied (The Plant Cell Physiology, 45: 1042-1052, 2004); however, DREB2 types have hardly been studied, and examples of known DREB2 orthologs are limited to Madagascar periwinkle ORCAI, rice OsDREB2A, and the like.

DREB1 genes have a conserved C/SEV/LR sequence in the AP2/ERF domain, and DREB2 genes have the AEIR sequence. Such difference is considered to differentiate their DNA-binding properties (The Plant Cell, 10: 1-17, 1998).

Plants that overexpress DREB1A, which is of the DREB1 type, exhibit improved tolerance to dehydration, salt, and low temperature stresses; however, plants that overexpress DREB2A, which is of the DREB2 type, or a rice ortholog thereof, OsDREB2A, do not express a clear phenotype or improved stress tolerance (The Plant Cell, 10:1-17, 1998). That is, activation of DREB2 types, which had been known, required some modification, such as deletion of a specific region.

DISCLOSURE OF THE INVENTION

The present invention is intended to identifying a DREB2 type maize-derived gene and providing a novel environmental stress tolerant plant through analysis of the function of such identified gene.

The present inventors succeeded in identifying a congenic DREB2A gene from maize and designated the same as "ZmDREB2A." Unlike DREB2A, ZmDREB2A exhibits the activity of a transcription factor without modification and improves the environmental stress tolerance of plants. Further, ZmDREB2A was found to improve high-temperature tolerance.

Specifically, the present invention relates to a gene encoding ZmDREB2A, which is a transcription factor derived from a maize. More specifically, such gene comprises the following DNA (a) or (b):

(a) DNA consisting of the nucleotide sequence as shown in SEQ ID NO: 1; or (b) maize-derived DNA hybridizing under stringent conditions with DNA consisting of a nucleotide sequence that is complementary to the DNA consisting of the nucleotide sequence as shown in SEQ ID NO: 1 and encoding a protein that regulates the transcription of a gene located downstream of a stress responsive element.

The gene of the present invention encodes the following protein (c) or (d):

(c) a protein consisting of the amino acid sequence as shown in SEQ ID NO: 2; or (d) a maize-derived protein consisting of an amino acid sequence derived from the amino acid sequence as shown in SEQ ID NO: 2 by deletion, substitution, or addition of one or several amino acids and regulating the transcription of a gene located downstream of a stress responsive element.

The gene of the present invention is capable of regulating the tolerance of a plant to environmental stress, such as dehydration, high-temperature, or salt stress.

The present invention also provides the recombinant protein (c) or (d) above.

Such recombinant protein can be obtained by introducing the gene of the present invention into an adequate host cell, allowing the gene to express therein, and recovering the resultant from a culture solution or the like.

The present invention also provides a recombinant vector comprising the gene of the present invention and a host cell or transgenic plant, which has been transformed with such vector.

A transgenic plant into which the gene of the present invention has been introduced and expressed at a high level exhibits improved tolerance to environmental stress, such as dehydration, high-temperature, or salt stress. The present invention also provides a method for improving the stress tolerance of a plant through the introduction of the gene of the present invention into such plant.

The ZmDREB2A gene of the present invention exhibits activity of a transcription factor without modification and can improve the environmental stress tolerance of plants, unlike known DREB2A or an ortholog thereof (e.g., OsDREB2A). Further, the ZmDREB2A gene can also improve high-temperature tolerance of plants.

BRIEF DESCRIPTION OF THE DRAWINGS

FIG. 1A shows a full-length nucleotide sequence of the long-form cDNA of ZmDREB2A. FIG. 1A shows a full-length cDNA sequence of ZmDREB2A comprising a portion that is considered to be an intron. An underlined portion indicates an intron.

FIG. 1B shows a nucleotide sequence and a putative amino acid sequence of the short-form cDNA of ZmDREB2A. The AP2 domain is underlined and indicated by red alphanumeric characters, and the nuclear transport signal is doubly underlined. Many acidic amino acids are present at the C terminus, and the C terminus is thus considered to be a transcriptional activation domain.

FIG. 2(A) shows the results of Northern analysis of the ZmDREB2A gene in maize. FIG. 2(B) shows the results of simultaneous amplification of the short-form cDNA and the long-form cDNA by RT-PCR. Two bands are observed at the time of the application of each form of stress (low temperature stress for 24 hours, high-temperature stress for 10 minutes, dehydration stress for 1 hour, and NaCl stress for 24 hours; D: the long-form positive control; B: the short-form positive control; N: the negative control).

FIG. 3 shows the results of expression analysis of long-form mRNA and short-form mRNA by RT-PCR (♦: long-form mRNA; ■: short-form mRNA; untreated long-form: 1). FIG. 3(A) shows the results of expression analysis of long-form mRNA and of short-form mRNA by RT-PCR; FIG. 3(B) shows the changed amount of long-form mRNA and that of short-form mRNA, represented by a chart indicating the change from the amount without stress application.

FIG. 6 shows the results of homology search of a partial amino acid sequence of ZmDREB2A. Pearl millet (*Pennisetum glaucum*: PgDREB2A), barley (*Hordeum vulgare*: HvDRF1), rice (*Oryza sativa*: OsDREB2B). Red prints indicate homologous portions=*: amino acid conserved by 4 sequences; .: amino acid conserved by 3 sequences.

FIG. 8 shows the characteristics of ZmDREB2A-overexpressing *Arabidopsis thaliana*. (A) The phenotype of ZmDREB2A-overexpressing *Arabidopsis thaliana*: morphology under common growth conditions was observed. The upper portion shows a plant that had been grown for 21 days on an agar medium; and the lower portion shows a plant 35 days after sowing. Such plant having been grown for 2 weeks on an agar medium and then transplanted to the soil (i.e., 15 days after transplantation). An empty vector-introduced strain was used as a wild-type strain. (B) Expression of ZmDREB2A and induced genes under each stress, low temperature stress was applied by placing the plant at 4° C., dehydration stress was induced by placing the plant extracted from the medium on a petri dish and treating the plant at room temperature therein. Salt stress was induced by placing the plant in 250 mM of NaCl for 5 hours.

FIG. 10 shows the high-temperature stress tolerance of ZmDREB2A-overexpressing *Arabidopsis thaliana* using the 35S promoter.

Figure 4:
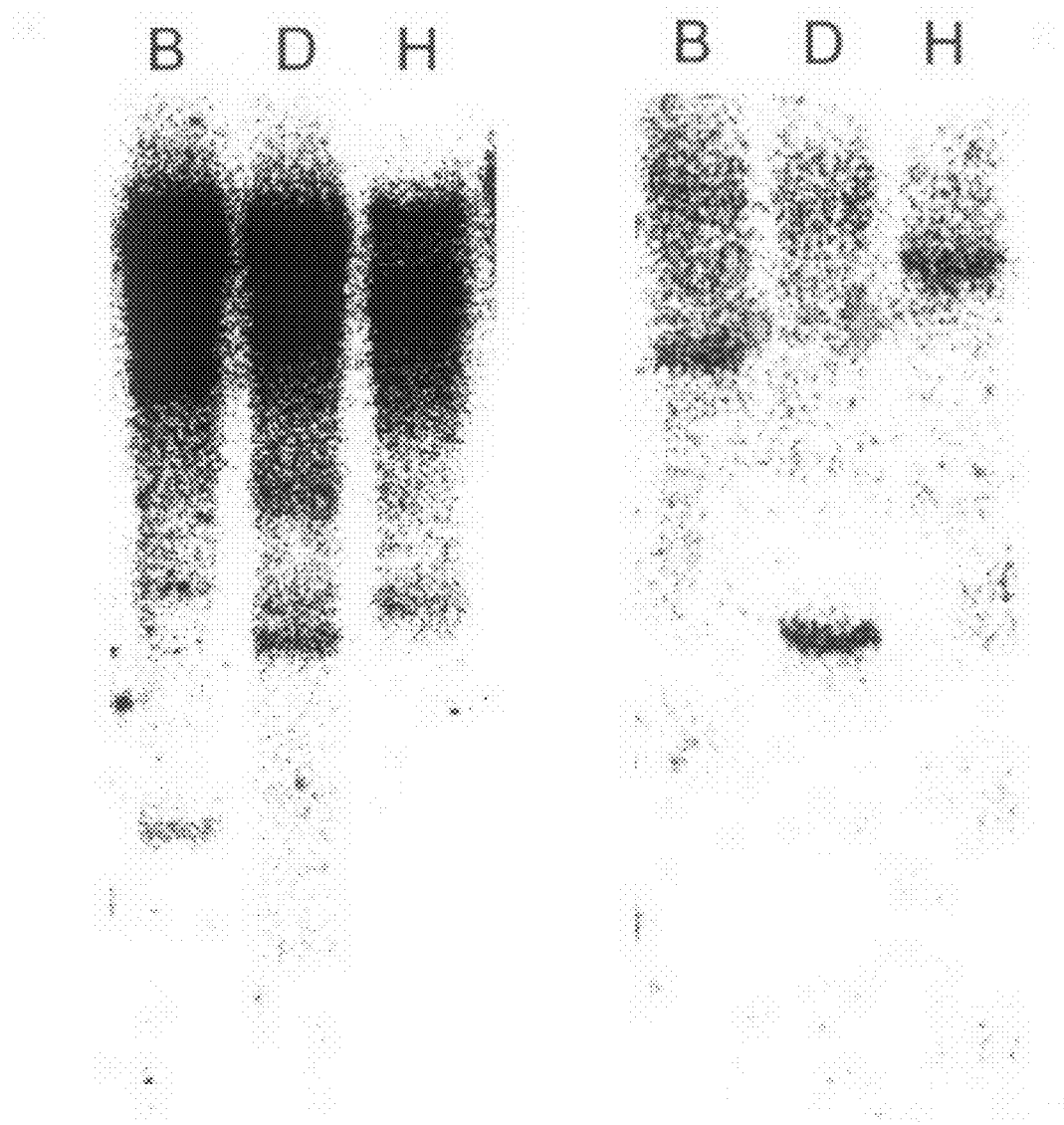
FIG. 4 shows the results of Southern analysis of the ZmDREB2A gene in maize: left: low stringency conditions (0.5% SSC, 0.5% SDS, 50° C.); right: high stringency conditions (0.1% SSC, 0.1% SDS, 65° C.).

This specification includes part or all of the contents as disclosed in the specification of Japanese Patent Application No. 2005-270970, which is a priority document of the present application.

BEST MODES FOR CARRYING OUT THE INVENTION

The gene of the present invention is a maize-derived gene encoding a transcriptional factor that binds to a cis element located upstream of genes encoding stress responsive proteins expressed in response to environmental stresses such as temperature, dehydration, or salt stress, thereby activating the transcription. Specific examples of the above cis element include dehydration-responsive element (DRE), abscisic acid-responsive element (ABRE), and low temperature-responsive element. The protein encoded by the gene of the present invention functions to activate the transcription of genes located downstream of the above-mentioned stress responsive elements (DRE and the like).

The gene according to the present invention can be identified as, for example, described below.

1. Identification of the Gene of the Present Invention

The gene according to the present invention can be screened for based on homology with a known gene having homologous functions; that is, a gene encoding a transcription factor specific to a stress tolerant gene of a plant. mRNA and cDNA libraries of maize or a maize genome library may be prepared and may be subjected to screening. Alternatively, an existing database of maize DNA may be subjected to screening.

The screened genes are subjected to adequate cloning and the entire nucleotide sequences thereof are determined in accordance with conventional methods. Nucleotide sequencing includes the chemical modification method of Maxam-Gilbert or the dideoxynucleotide chain termination method using an M13 phage. Usually, sequencing is carried out using an automated nucleotide sequencer (e.g., 377 DNA Sequencer, Perkin-Elmer).

Thus, 2 types of cDNAs (ZmDREG2A short-form: SEQ ID NO: 1; ZmDREB2A long-form: SEQ ID NO: 3) were isolated as maize-derived DREB2A orthologs. By analyzing the ORFs thereof, proteins encoded by the genes of interest, ZmDREB2A proteins (short form: SEQ ID NO: 2; long form: SEQ ID NO: 4), were identified. A longer cDNA (i.e., the long form) of the 2 identified types of cDNAs comprised a 53-bp intron, and the other cDNA (i.e., the short form) did not comprise the same. A frame shift took place in the long form due to the presence of the intron, and the encoded amino acid sequence was deduced to be very short. In contrast, the amino acid sequence encoded by the short form was deduced to be of a DREB2 type.

FIG. 1A shows the nucleotide sequence of the long-form cDNA and FIG. 1B shows the nucleotide sequence and the putative amino acid sequence of the short-form cDNA. As described below, the short-form cDNA functions as an active form of the ZmDREB2A gene, and such active ZmDREB2A gene (SEQ ID NO: 1) is referred to as the gene of the present invention.

The gene according to the present invention, however, is not limited to the gene comprising the nucleotide sequence as shown in SEQ ID NO: 1. A gene comprising DNA, which is hybridizable under stringent conditions with DNA comprising a nucleotide sequence that is complementary to the DNA comprising a nucleotide sequence as shown in SEQ ID NO: 1, is also the gene of the present invention as long as it encodes proteins that regulate the transcription of genes located downstream of a stress responsive element. Under "stringent conditions," hybridization is carried out with a formamide concentration of 30%-50% at 37° C. to 50° C. in a solution of 6×SSC. Preferably, hybridization is carried out with a formamide concentration of 50% at 42° C. in a solution of 6×SSC.

The genes of the present invention encode proteins comprising amino acid sequences as shown in SEQ ID NO: 2. Even though a protein comprises an amino acid sequence derived from the amino acid sequence as shown in SEQ ID NO: 2 by deletion, substitution, or addition of one or several amino acids, genes encoding such proteins are within the scope of the genes of the present invention, as long as such protein can regulate the transcription of genes located downstream of a stress responsive element. The term "several amino acids" preferably refers to 20 or fewer and more preferably 5 or fewer amino acids.

The introduction of mutation into the gene of the present invention may be performed by conventional techniques such as the Kunkel method, the gapped duplex method or variations thereof using a mutation introducing kit (e.g. Mutant-K (Takara) or Mutant-G (Takara)) utilizing site-directed mutagenesis or using an LA PCR in vitro Mutagenesis Series Kit (Takara), for example.

Once the nucleotide sequence for the gene of the present invention has been determined, the gene of the present invention can be obtained either by chemical synthesis, by PCR using the cDNA or genomic DNA of the gene as a template, or by the hybridization of a DNA fragment having the above nucleotide sequence as a probe.

2. Analysis of the DRE Binding Ability and Transcription Activating Ability of the Proteins of the Present Invention (1) Analysis of the DRE Binding Ability The ability of the protein according to the present invention to bind to DRE can be confirmed by gel shift assay (Urao, T. et al., Plant Cell 5: 1529-1539, 1993) using a fusion protein composed of the protein, GST, and the like. The protein according to the present invention can be prepared by ligating the gene according to the present invention downstream of the glutathione-S-transferase (GST) coding region of a plasmid coding for the GST gene (e.g. pGEX-4T-1 vector: Pharmacia) in a manner such that the reading frames of the two genes coincide with each other, culturing E. coli that has been transformed with the plasmid under conditions that induce synthesis of the fusion protein, and purifying the protein from the transformed E. coli.

Gel shift assay is a method for examining the interaction between DNA and a protein. A DRE-containing DNA fragment labeled with $^{32}P$ or the like is mixed with the fusion protein described above and incubated, and the resultant mixture is subjected to electrophoresis. After drying, the gel is autoradiographed to detect those bands that have migrated to the back as a result of the binding of the DNA fragment and the protein. The specific binding of the protein according to the present invention to the DRE sequence can be confirmed by showing that the above-mentioned band is not detected when a DNA fragment containing a mutated DRE sequence is used.

(2) Analysis of Transcription Activating Ability

The transcription activating ability of the proteins of the present invention can be analyzed by a transactivation experiment using a maize protoplast system. For example, ZmDREB2A cDNA is ligated to pBI221 plasmid (Clontech) containing CaMV35S promoter to construct an effector plasmid. On the other hand, the DRE-containing DNA fragment is ligated upstream of TATA promoter located upstream of a β-glucuronidase (GUS) gene to construct a reporter plasmid. Subsequently, these two plasmids are introduced into maize protoplasts and then GUS activity is measured. If GUS activity is increased by the simultaneous expression of the ZmDREB2A protein, it is understood that the ZmDREB2A protein expressed in the protoplasts is activating the transcription through the DRE sequence.

In the present invention, preparation of protoplasts and introduction of plasmid DNA into the protoplasts may be performed by the method of Abel et al. (Abel, S. et al., Plant J. 5: 421-427, 1994). In order to minimize experimental errors resulting from differences in plasmid DNA introduction efficiencies, a plasmid in which a luciferase gene is ligated downstream of CaMV35S promoter may be introduced to protoplasts together with the two plasmids described above, and β-glucuronidase activity against luciferase activity may be determined. Then, the determined value may be taken to indicate transcription activating ability. β-glucuronidase activity can be determined by the method of Jefferson et al. (Jefferson, R. A. et al., EMBO J. 83: 8447-8451, 1986); and luciferase activity can be determined using PicaGene Luciferase Assay Kit (Toyo Ink).

3. Preparation of Recombinant Vectors and Transformants (1) Preparation of Recombinant Vectors The recombinant vector of the present invention can be obtained by ligating (inserting) the gene of the present invention to (into) an appropriate vector. The vector into which the gene of the present invention is to be inserted is not particularly limited as long as it is replicable in a host. For example, plasmid DNA, phage DNA, or the like may be used. Plasmid DNA includes: plasmids for E. coli hosts such as pBR322, pBR325, pUC118, and pUC119; plasmids for Bacillus subtilis hosts such as pUB110 and pTP5; plasmids for yeast host such as YEp13, YEp24, and YCp50; and plasmids for plant cell host such as pBI221 and pBI121. Phage DNA includes λ phage and the like. Further, an animal virus vector such as a retrovirus or vaccinia virus vector or an insect virus vector such as a baculovirus vector may also be used.

In order to insert the gene of the present invention into a vector, for example, a method may be employed in which the purified DNA is cleaved with an appropriate restriction enzyme and then inserted into the restriction site or the multicloning site of an appropriate vector DNA for ligation to the vector. The gene of the present invention should be incorporated into the vector in such a manner that the function of the gene is expressed. For this purpose, in addition to a promoter and the gene of the present invention, those containing cis elements such as enhancer, a splicing signal, poly(A) addition signal, selection marker, ribosome binding sequence (SD sequence) or the like can be ligated to the vector of the present invention, if so desired. Examples of selection marker are dihydrofolate reductase gene, ampicillin tolerance gene, neomycin tolerance gene, and the like.

(2) Preparation of Transformants

The transformant of the present invention can be obtained by introducing the recombinant vector of the present invention into a host so that the gene of interest can be expressed. The host is not particularly limited as long as the gene of the present invention can be expressed therein. Specific examples of the host include *Escherichia* bacteria such as *E. coli; Bacillus* bacteria such as *Bacillus subtilis; Pseudomonas* bacteria such as *Pseudomonas putida; Rhizobium* bacteria such as *Rhizobium meliloti*; yeasts such as *Saccharomyces cerevisiae* and *Schizosaccharomyces pombe*; plant cell strains established from *Arabidopsis thaliana*, tobacco, maize, rice, or carrot, etc., or protoplasts prepared from such plants; animal cells such as COS cells and CHO cells; and insect cells such as Sf9 cells and Sf21 cells.

When a bacterium such as *E. coli* is used as the host, the recombinant vector of the present invention is capable of autonomous replication inside the host and, at the same time, it is preferably composed of a promoter, a ribosome binding sequence, the gene of the present invention, and a transcription termination sequence. The vector may also contain a gene to regulate the promoter. *Escherichia coli* strains such as HMS174 (DE3), K12, or DH1 may be used. *Bacillus subtilis* strains such as MI 114 or 207-21 may be used.

Any promoter may be used as long as it is able to direct the expression of the gene of interest in a host such as *E. coli*. For example, an *E. coli*- or phage-derived promoter such as trp promoter, lac promoter, $P_L$ promoter, or $P_R$ promoter may be used. An artificially designed and altered promoter such as tac promoter may also be used. Methods for introducing the recombinant vector into a bacterium are not particularly limited, and examples thereof include a method using calcium ions (Cohen, S, N. et al., Proc. Natl. Acad. Sci., USA, 69: 2110-2114, 1972) and electroporation.

When yeast such as *Saccharomyces cerevisiae, Schizosaccharomyces pombe*, or *Pichia pastoris* is used as the host, the promoter is not particularly limited, and any promoter may be used as long as it is able to direct the expression of the gene of interest in yeast. For example, gall promoter, gal10 promoter, heat shock protein promoter, MFα1 promoter, PH05 promoter, PGK promoter, GAP promoter, ADH promoter, or AOX1 promoter can be used.

A method for introducing the recombinant vector into yeast is not particularly limited, and examples thereof include electroporation (Becker, D. M. et al., Methods Enzymol., 194: 182-187, 1990), the spheroplast method (Hinnen, A. et al., Proc. Natl. Acad. Sci., USA, 75: 1929-1933, 1978), and the lithium acetate method (Itoh, H., J. Bacteriol., 153: 163-168, 1983).

When a plant cell is used as the host, for example, cell strains established from rice, maize, wheat, *Arabidopsis thaliana*, tobacco, carrot, etc. or protoplasts prepared from such plants are used. In this case, the promoter to be used is not particularly limited as long as it is able to direct the expression of the gene of interest in plants. Examples thereof include 35S RNA promoter of cauliflower mosaic virus, rd29A gene promoter, and rbcS promoter.

A method for introducing the recombinant vector into a plant includes the method of Abel et al. using polyethylene glycol (Abel, H. et al., Plant J. 5: 421-427, 1994) and electroporation. When an animal cell is used as the host, for example, simian COS-7 or Vero cells, Chinese hamster ovary cells (CHO cells), mouse L cells, rat GH3 cells, human FL cells, or the like and SRα promoter, SV40 promoter, LTR promoter, CMV promoter, or the like may be used. The early gene promoter of human cytomegalovirus or the like may also be used.

To introduce the recombinant vector into an animal cell, for example, electroporation, the calcium phosphate method, lipofection, or the like may be used. When an insect cell is used as the host, for example, Sf9 cells, Sf21 cells, or the like may be used. The recombinant vector may be introduced into an insect cell by the calcium phosphate method, lipofection, electroporation, or the like.

4. Production of the Recombinant Proteins According to the Present Invention

The recombinant protein of the present invention is a protein that has an amino acid sequence encoded by the gene of the present invention or a protein that has an amino acid sequence having at least one amino acid mutation in the above-described amino acid sequence and is able to regulate the transcription of genes located downstream of a stress responsive element.

The protein of the present invention can be obtained by culturing the transformant in a medium and recovering the protein from the resultant culture product. The term "culture product" means any of the following materials: culture supernatant, cultured cells, cultured microorganisms, or disrupted cells or microorganisms. The transformant of the present invention in a medium is cultured by conventional methods for culturing a host.

As a medium for culturing the transformant obtained from a microorganism host such as *E. coli* or yeast, either a natural or synthetic medium may be used as long as it contains carbon sources, nitrogen sources, and inorganic salts assimilable by the microorganism and is capable of efficient culture of the transformant. When a plant cell is used as the host, vitamins such as thiamine and pyridoxine can be added to the medium, if necessary. When an animal cell is used as the host, serum such as RPMI1640 can be added to the medium, if necessary.

Examples of carbon sources include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor.

Examples of inorganic substances include: monopotassium phosphate, dipotassium phosphate, magnesium phosphate, magnesium sulfate, sodium chloride, iron(I) sulfate, manganese sulfate, copper sulfate, and calcium carbonate. Usually, culture is carried out under aerobic conditions (such as shaking culture or aeration agitation culture) at approximately 30° C. to 37° C. for approximately 6 hours to 3 days. During culture, the pH is maintained at approximately 7.0 to 7.5. The pH is adjusted with an inorganic or organic acid, an alkali solution, or the like.

During culture, an antibiotic such as ampicillin or tetracycline may be added to the medium, if necessary. When a microorganism transformed with an expression vector containing an inducible promoter is cultured, an inducer may be added to the medium, if necessary. For example, when a microorganism transformed with an expression vector containing Lac promoter is cultured, isopropyl-β-D-thiogalactopyranoside (IPTG) or the like may be added to the medium. When a microorganism transformed with an expression vector containing trp promoter is cultured, indoleacrylic acid (IAA) or the like may be added to the medium.

Usually, the culture is carried out in the presence of 5% $CO_2$ at approximately 30° C. to 37° C. for approximately 6 hours to 3 days. During culture, an antibiotic such as kanamycin or penicillin may be added to the medium if necessary. After the culture, the protein of the present invention is extracted by disrupting the cultured microorganism or cell if the protein is produced in the microorganism or cell. If the protein of the present invention is secreted outside of the microorganism or cell, the culture fluid may be used for the following steps as it is or after being subjected to centrifugation to remove the microorganism or cells. Thereafter, conventional biochemical techniques used for isolating/purifying a protein, for example, ammonium sulfate precipitation, gel chromatography, ion exchange chromatography, and affinity chromatography, are employed independently or in an appropriate combination to isolate and purify the protein of the present invention from the above culture product.

5. Preparation of Transgenic Plants into which the Gene of the Present Invention has been Introduced A transgenic plant tolerant to environmental stresses, and in particular, high-temperature and dehydration stresses, can be produced by introducing DNA encoding the protein of the present invention into a host plant via genetic engineering techniques. A method for introducing the gene of the present invention into a host plant includes indirect introduction such as the *Agrobacterium* infection method and direct introduction such as the particle gun method, the polyethylene glycol method, the liposome method, and the microinjection method. When the *Agrobacterium* infection method is used, the transgenic plant of the present invention can be produced by the following procedure.

(1) Preparation of a Recombinant Vector to be Introduced into a Plant and Transformation of *Agrobacterium*

A recombinant vector to be introduced into a plant can be prepared by cleaving DNA comprising the genes of the present invention with an appropriate restriction enzyme, ligating an appropriate linker to the resultant DNA if necessary, and inserting the DNA into a cloning vector for the plant cell host. A binary vector type plasmid such as pBI2113Not, pBI2113, pBI101, pBI121, pGA482, pGAH, or pBIG, or an intermediate vector type plasmid such as pLGV23Neo, pNCAT, or pMON200 may be used as cloning vectors.

When a binary vector type plasmid is used, the gene of interest is inserted between the border sequences (LB, RB) of the binary vector. The resultant recombinant vector is amplified in *E. coli*. The amplified recombinant vector is then introduced into *Agrobacterium tumefaciens* C58, LBA4404, EHA101, C58C1Rif$^R$, EHA105, etc. by freeze-thawing, electroporation, or the like. The resultant *Agrobacterium* is used for the transformation of the plant of interest.

In the present invention, the three-member conjugation method (Nucleic Acids Research, 12: 8711, 1984) may also be used in addition to the method described above to prepare an *Agrobacterium* containing the gene of the present invention for plant infection. Specifically, plasmid-containing *E. coli* comprising the gene of interest, helper plasmid-containing *E. coli* (e.g. pRK2013), and an *Agrobacterium* are mixed and cultured on a medium containing rifampicilin and kanamycin. Thus, a zygote *Agrobacterium* for infecting plants can be obtained.

For the expression of a foreign gene and the like in a plant body, a promoter and a terminator for plants should be located upstream and downstream of the structural gene, respectively. Specific examples of promoters that may be utilized in the present invention include cauliflower mosaic virus (CaMV)-derived 35S transcript (Jefferson, R. A. et al., The EMBO J. 6: 3901-3907, 1987); the promoter for maize ubiquitin gene (Christensen, A. H. et al., Plant Mol. Biol. 18: 675-689, 1992); the promoter for nopaline synthase (NOS) gene; and the promoter for octopin (OCT) synthase gene. Specific examples of useful terminators include CaMV-derived terminators and NOS-derived terminators. Promoters and terminators are not limited to the above-mentioned examples as long as they are known to function in plant bodies.

If the promoter used in a transgenic plant is a promoter responsible for the constitutive expression of the gene of interest (e.g. CaMV 35S promoter) and the use thereof has brought about delay in the growth or retardation of the transgenic plant, a promoter that directs transient expression of the gene of interest (e.g. rd29A gene promoter) may be used. If necessary, an intron sequence that enhances the expression of the gene of the present invention may be located between the promoter sequence and the gene. For example, the intron from maize alcohol dehydrogenase (Adh1) (Genes & Development 1: 1183-1200, 1987) may be introduced.

In order to efficiently select transformed cells of interest, it is preferable to use an effective selection marker gene in combination with the gene of the present invention. As a selection marker, one or more genes selected from the kanamycin tolerance (NPTII) gene, the hygromycin phosphotransferase (htp) gene, which confers tolerance to the antibiotic hygromycin on plants, the phosphinothricin acetyl transferase (bar) gene, which confers tolerance to bialaphos, and the like can be used. The gene of the present invention and the selection marker gene may be incorporated together into a single vector. Alternatively, two types of recombinant DNAs incorporated into separate vectors may be used.

(2) Introduction of the Gene of the Present Invention into a Host

In the present invention, while the host for the transformant is not particularly limited, it is preferably a plant. The plant may be composed of any cultured plant cells, the entire plant body of a cultured plant, plant organs (such as leaves, petals, stems, roots, rhizomes, or seeds), or plant tissues (such as epidermis, phloem, parenchyma, xylem, or vascular bundle). Plants are preferably monocotyledonous plants such as rice, maize, and wheat. When a cultured plant cell, plant body, plant organ, or plant tissue is used as the host, the *Agrobacterium* infection method, particle gun method, or polyethylene glycol method can be employed to introduce the DNA encoding the protein of the present invention to transform this host plant by introducing a vector into plant sections. Alternatively, a vector can be introduced into a protoplast by electroporation to produce a transformed plant.

For example, when a gene is introduced into *Arabidopsis thaliana* by the *Agrobacterium* infection method, the step of infecting the plant with an *Agrobacterium* containing a plasmid comprising the gene of interest is essential. This step can be performed by the vacuum infiltration method (CR Acad. Sci. Paris, Life Science, 316: 1194, 1993). Specifically, *Arabidopsis thaliana* is grown in soil composed of equivalent portions of vermiculite and perlite. The *Arabidopsis thaliana* is immersed directly in a culture fluid of an *Agrobacterium* containing a plasmid comprising the gene of the present invention, the grown maize is placed in a desiccator, and the resultant is then sucked with a vacuum pump to 65-70 mmHg. Then, the plant is allowed to stand at room temperature for 5-10 min. The plant pot is transferred to a tray, which is covered with a wrap to maintain humidity. On the next day, the wrap is removed. The plant is grown in such state to harvest seeds.

Subsequently, the seeds are sown on MS agar medium supplemented with appropriate antibiotics to select those plants that have the gene of interest *Arabidopsis thaliana* plants grown on this medium are transferred to pots and grown there. As a result, seeds of a transgenic plant into which the gene of the present invention has been introduced can be obtained. Generally, the genes are introduced into the genome of the host plant in a similar manner. However, due to differences in the specific locations on the genome into which the genes have been introduced, the expression of the introduced genes varies. This phenomenon is called "position effect." By assaying transformants with DNA fragments from the introduced gene as a probe by Northern blotting, it is possible to select those transformants in which the introduced gene is expressed at a higher level.

The confirmation that the gene of interest has been integrated into the transgenic plant into which the gene of the present invention has been introduced and into the plants of the subsequent generation thereof can be made by extracting DNA from cells and tissues of those plants and detecting the introduced gene by PCR or Southern analysis, which are conventional methods in the art.

(3) Analysis of the Expression Level and Expression Site of the Gene of the Present Invention in Plant Tissues The expression level and expression site of a gene in a transgenic plant into which the gene of the present invention has been introduced can be analyzed by extracting RNA from cells and tissues of the plant and detecting the mRNA of the introduced gene by RT-PCR or Northern analysis, which are conventional methods in the art. Alternatively, the expression level and expression site can be analyzed directly by Western blotting or the like of the gene product of the present invention using an antibody against the above product.

(4) Changes in the mRNA Levels of Various Genes in a Transgenic Plant into which the Gene of the Present Invention has been Introduced It is possible to identify by Northern hybridization those genes whose expression levels are believed to have been changed as a result of the action of the transcription factor of the present invention in a transgenic plant into which the gene of the present invention has been introduced.

For example, plants grown hydroponically or the like are subjected to environmental stress for a specific period of time (e.g., 1 to 2 weeks). Examples of environmental stresses include high-temperature, dehydration, and salt stresses. For example, dehydration stress may be imposed by uprooting the plant from the hydroponic medium and drying it on a filter paper for 10 minutes to 24 hours. High-temperature stress may be imposed by retaining the plant at 30° C. to 50° C. for 10 minutes to 24 hours. Salt stress can be imposed by, for example, replacing the hydroponic medium with a 50 to 500 mM NaCl solution and retaining the plant for 10 minutes to 24 hours.

Total RNAs are separately prepared from a control plant that was subjected to no stress, and from a plant that was subjected to environmental stress, and the resultant total RNAs are subjected to electrophoresis. The expression patterns can be analyzed by Northern hybridization using the probe of the gene to be observed.

(5) Evaluation of the Tolerance of the Transgenic Plant to Environmental Stresses The tolerance to environmental stresses of the transgenic plant into which the gene of the present invention has been introduced can be evaluated by setting the transgenic plant in a pot containing a soil comprising vermiculite, perlite and the like, exposing the plant to various environmental stresses, and examining the survival of the plant. Environmental stresses include high-temperature, dehydration, and salt stresses. For example, tolerance to dehydration stress can be evaluated by leaving the plant without watering for 2 to 4 weeks and then examining the survival. Tolerance to high-temperature stress can be evaluated by leaving the plant at 30° C. to 50° C. for 30 minutes to 10 days, growing it at 20° C. to 35° C. for 2 days to 3 weeks, and then examining its survival ratio. Tolerance to salt stress can be evaluated by, for example, leaving the plant in 100 to 600 mM NaCl for 1 hour to 7 days, growing it at 20° C. to 35° C. for 1 to 3 weeks, and then examining its survival rate.

6. Determination of Stress Levels in Plants

The transcription of the gene according to the present invention is activated by low-temperature stress, dehydration stress, salt stress, or high-temperature stress. Therefore, determination of the transcription level of the gene of the present invention enables the assessment of the stress level, such as regarding low-temperature stress, dehydration stress, salt stress, or high-temperature stress to which the plant is subjected.

The transcription level of the gene according to the present invention can be determined by, for example, RNA gel blot analysis, or quantitative PCR. A probe to be used in RNA gel blot analysis can be produced in accordance with any conventional method based on the gene according to the present invention and/or a 100-1000 bp region comprising a specific sequence adjacent to the gene. A primer to be used in quantitative PCR can be prepared by any conventional method based on the sequence in the region encoding the gene of the present invention or the region adjacent thereto.

The above-described probe or primer may be used in a kit for determining the transcription level of the gene according to the present invention.

7. Others

In addition, the protein according to the present invention can be utilized by producing an antibody against the protein. The antibody may be a polyclonal or monoclonal antibody. The method for producing an antibody is not particularly limited, and it can be carried out in accordance with any conventional method (see, for example, Sambrook, J et al., Molecular Cloning, Cold Spring Harbor Laboratory Press, 1989). The antibody can be utilized in, for example, the detection of the protein of interest by Western blotting or immunoprecipitation.

EXAMPLES

The present invention is described in greater detail with reference to the following examples, although the scope of the present invention is not limited thereto.

Example 1

Isolation of ZmDREB2A Gene

1. Database Homology Search

Based on the sequence of the AP2/ERF domain, homology search was carried out using BLAST on maize DNA databases of GenBank, and several EST sequences were obtained. Based on the longest EST sequence, the following primers for RT-PCR were designed, and two types of cDNAs were obtained from maize RNA via RT-PCR. Primers for isolating ZmDREB2A AY108198 Forward: 5'-GGTCTTATCGACTCCAACAAGAAC-3' (SEQ ID NO: 5)

AY108198 Reverse: 5'-AAAAGCAAGCACTCTTTTTA-3' (SEQ ID NO: 6)

The obtained full-length cDNA of ZmDREB2A was subjected to nucleotide sequencing using the 377 DNA Sequencer (Perkin-Elmer). Further, ORF was analyzed to determine all the amino acid sequences.

As a result, the nucleotide sequence of the ZmDREB2A gene (short-form: SEQ ID NO: 1, long-form: SEQ ID NO: 3) and the corresponding amino acid sequence of ZmDREB2A protein (short-form: SEQ ID NO: 2, long-form: SEQ ID NO: 4) were identified. The longer cDNA of the two identified types of cDNAs (i.e., the long form) comprised a 53-bp intron, and the shorter cDNA (i.e., the short form) did not comprise the intron. In the long-form cDNA, a frame shift took place in the intron, and ORF was very short. The short-form cDNA exhibited a DREB-type structure. FIG. 1A shows the nucleotide sequence of long-form cDNA and FIG. 1B shows the nucleotide sequence of the short-form cDNA and a putative amino acid sequence thereof. As described below, this short-form cDNA functions as an active form of the ZmDREB2A gene.

Example 2

Analysis of ZmDREB2A Gene Expression in Non-Transgenic Plant

Expression characteristics of the ZmDREB2A gene in maize were analyzed via Northern analysis, RT-PCR, and Southern analysis.

1. Materials and Method (1) Conditions for Maize Cultivation

Seeds of maize (variety: Golden Cross Bantam) were treated with 70% ethanol for 5 minutes, thoroughly washed with water, and placed on a stainless steel mesh. The mesh was introduced into a pan containing water, and the seeds were grown in an incubator at 26° C. with a photoperiod of 12 hours.

(2) Stress Application

Plants that had been hydroponically grown for 1 week were subjected to the following stress applications.

Low temperature stress: the stainless steel mesh having seeds thereon was transferred to water that had been cooled to 4° C. in advance, and the resultant was treated in that state in an incubator at 4° C.

High-temperature stress: the stainless steel mesh having seeds thereon was transferred to water that had been heated to 42° C. in advance, and the resultant was treated in that state in an incubator at 37° C.

Salt stress: the stainless steel mesh having seeds thereon was treated with a 250 mM NaCl solution, and the resultant was treated in an incubator at 26° C.

Dehydration stress: the plants were patted and dried on a KimTowel after the roots were thoroughly drained.

These plants were treated for 0 minutes, 10 minutes, 20 minutes, 40 minutes, 1 hour, 2 hours, 5 hours, and 24 hours, recovered, immediately frozen in liquid nitrogen, and then stored at −80° C.

(3) RNA Extraction

While the plants, which had been subjected to stress, were maintained in a frozen state, they were disrupted using the shake master (BMS-12, Tommy), and RNA was extracted using a Trizol liquid (Invitrogen) in accordance with a conventional technique.

(4) Northern Analysis

The extracted RNA (6 μg) was isolated, 19 μl of Northern dye (0.1% BPB, 1×RNA electrophoresis buffer, 20% formaldehyde, 60% formamide, 0.033 μg/μl EtBr) was added thereto, and the resultant was treated at 65° C. for 15 minutes, followed by quenching for denaturation.

The prepared RNA was applied to a gel, and the resultant was electrophoresed in 1×RNA electrophoresis buffer (0.02 M MOPS, 8 mM sodium acetate, 1 mM EDTA) at 90 V for 2.5 hours. The product was transferred to a nylon membrane (Hybond-XL, Amersham) using 20×SSC overnight, air-dried for 1 hour, and treated under reduced pressure at 80° C. for 2 hours.

Primers were prepared in a manner such that an about 500-bp region at the C-terminus specific for ZmDREB2A became a probe. Primer sequences are as shown in Table 1. Using these primers, probes were prepared by PCR. The composition of the PCR solution (total amount: 20 μl) was as shown below, and the solution was prepared in accordance with the protocol of the KOD DNA polymerase plus (TOYOBO).

| Reaction condition | |
|---|---|
| 10× buffer | 2.0 μl |
| 2 mM dNTPs | 2.0 μl |
| 25 mM MgCl$_2$ | 0.8 μl |
| 10 pmol forward primer | 1.0 μl |
| 10 pmol reverse primer | 1.0 μl |
| Plasmid DNA solution | 1.0 μl |
| KOD plus polymerase | 0.4 μl |

PCR Conditions

95° C. for 5 minutes

95° C. for 15 seconds, 60° C. for 30 seconds, and 68° C. for 30 seconds×25 cycles 68° C. for 7 minutes The band was confirmed via electrophoresis, cleaved, and purified. The purified band was labeled with the BcaBEST Labeling Kit (TaKaRa) and used as a probe. Distilled water was added to a mixture of 2 μl of random primer, and 25 ng of template DNA solution for probe to bring the total amount to 14 μl. The resultant was heated at 95° C. for 3 minutes, and the resultant was then quenched in ice for 5 minutes for denaturation. 10× buffer (2.5 μl), dNTP (2.5 μl), DNA polymerase (1 μl), and [α-$^{32}$P] dCTP (5 μl) were added thereto, and the mixture was treated at 55° C. for 10 minutes. After the reaction, the reaction product was applied to the Sephadex G50 column (Pharmacia) to separate a labeled probe from free [α-$^{32}$P] dCTP.

The membrane to which RNA has been transferred was introduced into a glass tube, the membrane was washed with distilled water and a 5×SSC solution (80 mM NaCl and 80 mM sodium citrate), 30 ml of a hybridization buffer (0.5 M Na$_2$HPO$_4$.12H$_2$O, 0.5M NaH$_2$PO$_4$.2H$_2$O, 7% SDS, and 10 mM EDTA) was added thereto, and prehybridization was carried out at 65° C. for at least 30 minutes. Subsequently, the solution was discarded, labeled probes were added to 30 ml of a fresh hybridization buffer to a concentration of 1.0×10$^6$ dpm/ml, and hybridization was carried out at 65° C. overnight.

The membrane was washed with a washing solution 1 (1×SSC and 1×SDS) at 65° C. for 5 minutes and then with a washing solution 2 (0.1×SSC and 0.1×SDS) twice for 30 minutes and once for 5 minutes. After the membrane was air-dried for at least 1 hour, the signal was detected. Signal analysis was carried out using the BAS2000 Imaging Analyzer (Fiji Film).

(5) Quantitative RT-PCR Analysis

The difference between the length of the long form and that of the short form is only 53 bp. Accordingly, signals cannot be distinguished via Northern analysis. In order to separately analyze each expression, therefore, primers specific for the long form and for the short form were prepared and quantitative RT-PCR analysis was carried out.

cDNA was synthesized using the ReverTra Ace kit (Toyobo). Table 1 shows the sequences of primers specific for the long-form cDNA and for the short-form cDNA.

As an apparatus for quantitative RT-PCR, the Light Cycler (Roche) was used, and SYBR Green Ex taq (TaKaRa) was used as a reaction reagent. 2×SYBR (5 µl), 2 µmol of the forward primer, 2 µmol of the reverse primer, and 3.5 µl of MilliQ water were added to template cDNA (1 µl of ZmDREB2A and 0.001 µl of 18 SrRNA), and the reaction was allowed to proceed. 18 SrRNA was used as an internal standard. Table 1 shows the sequences of primers used.

TABLE 1

| | Names of primers | Sequences (5' → 3') |
|---|---|---|
| Northern | | |
| ZmDREB2A | AY108198-probe-for | GGGTCTAGAATGCCGATGCAGCCCC |
| | AY108198-probe-rev | GGGGGATCCTCAGTTTAGCCGCTCC |
| RT-PCR | | |
| 18SrRNA | 18SrRNA forward | AAACGGCTACCACATCCAAG |
| | 18SrRNA reverse | CCTCCAATGGATCCTCGTTA |
| rd29A | rd29A forward | TGGACACGAATTCTCCATCA |
| | rd29A reverse | TTCCAGCTCAGCTCCTGATT |
| Long form | AY108198-longer156F | GATGACAGCTGCCACTGACGTA |
| | AY008198-longer128R | CGTAGGCCCATCTCGTGATC |
| Short form | AY108198-shorter24F | GCAGCCCGGAAGGAAGAA |
| | AY108198-shorter90R | GATGACAGCTGCCACTGACGAT |

* From top to bottom, the primer sequences shown in Table 1 are those of SEQ ID NOs: 7 to 16 in the Sequence Listing.

PCR Conditions
95° C. for 10 seconds
95° C. for 5 seconds, 60° C. for 20 seconds and 74° C. for 5 seconds×40 cycles Subsequently, amplification of the putative nucleotide sequence was confirmed by analyzing the melting temperature of the amplification product.

In order to quantify the expression levels, pBlueScript vector comprising the long-form and short-form cDNAs of known concentrations incorporated therein was used to prepare a calibration curve. The concentration determined based on such calibration curve was divided by an internal standard to determine relative expression levels.

(6) Southern Analysis

Genomic Southern analysis was carried out in order to determine the number of ZmDREB2A copies of the maize genome.

The primers and the kit used were the same as those used in (4) above. Genomic DNA was extracted from a maize leaf in accordance with the CTAB method.

Extracted DNA (10 µg) was treated with 10 µl each of BamHI, DraI, and HindIII restriction enzymes (TaKaRa) at 37° C. overnight. DNA was recovered from the solution via ethanol precipitation and dissolved in 300 µl of TE solution. The product was electrophoresed on 1% agarose gel (1×TBE) at 70 V for 6.5 hours. The resultant was successively subjected to denaturation with the aid of an acidic solution (0.25N HCl), a denaturing solution (0.5N NaOH and 1.5 M NaCl), and a neutralizing solution (0.5 M Tris-HCl and 1.5 M NaCl) in that order, and the denatured product was transferred to a nylon membrane (Amersham) overnight.

The membrane onto which the denatured product had been transferred was subjected to hybridization with a probe. The same probe as that used in Northern analysis was used. Such procedures are in accordance with those of Northern analysis; however, washing was carried out in 2 ways as below:
under low stringency conditions: 0.5×SSC, 0.5×SDS, 50° C. (twice for 30 minutes);
under high stringency conditions: 0.1×SSC, 0.1×SDS, 65° C. (twice for 30 minutes).

2. Results (1) Northern Analysis

Plants that had been hydroponically cultivated for 1 week after sowing were subjected to various types of stress application, and RNA extracted from such plants were used to conduct an experiment. Expression analysis was carried out by the Northern method using ZmDREB2A-specific regions as probes (FIG. 2A). When low temperature stress was applied to ZmDREB2A, induction of expression was observed 2 hours later, and considerably strong expression was observed 5 hours later. When high-temperature stress was applied, induction of expression was observed with treatment at 42° C. In the case of induction of expression by high temperature, it was confirmed that strong expression was induced by 10 to 20 minutes of treatment and that the expression level was gradually lowered thereafter. When dehydration stress was applied, constant and weak expression was observed; however, the level of expression induction was not significant. When salt stress was applied, somewhat strong expression was observed in the root 10 minutes after the application of stress, and expression became stronger with the elapse of time.

Expression of ZmDREB2A was mainly observed in the root upon each type of stress application, and expression was not significant in the stem and in the leaf. However, induction of expression was observed in the leaf upon low-temperature and high-temperature stress application.

This demonstrates that expression of ZmDREB2A is induced upon stress application and that the expression patterns thereof vary depending on the type of stress.

(2) Quantitative RT-PCR Analysis

The forward primer of the short-form cDNA comprises a sequence partially homologous to that of the long-form cDNA. These primers were confirmed to function in a sequence-specific manner. The long-form cDNA and the short-form cDNA were used as templates, PCR was carried out by adding these primers, and the reaction solution was electrophoresed on 2% agarose gel. As a result, these primers were found to amplify sequences in a template-specific manner.

The identical primers (AY108198 cDNA BamHI and AY108198 shorter R90) were provided outside the intron, and two fragments of different length were simultaneously amplified. Thus, whether or not 2 types of mRNAs were actually accumulated was confirmed (FIG. 2B). Except for the control, formation of 2 electrophoresis bands was observed upon each type of stress application. Since both long-form and short-form cDNAs develop bands at the same position with the positive control, such bands were confirmed to be of long-form and short-form cDNAs, and the presence of 2 types of clones was confirmed.

Further, changes in mRNA accumulation over time were analyzed (FIGS. 3A and 3B). Without stress application, substantially no expression was observed in both mRNAs. When the long-form mRNA was compared with the short-form mRNA, the amount of the long-form mRNA was found to be about 1,000 times more than that of the short-form mRNA. Expression thereof was induced by stress application. As a whole, the expression level of the long-form mRNA was higher, the expression level of the short-form mRNA became very high upon stress application, and the amount of accumulated short-form mRNA was occasionally greater than that of the long-form mRNA, such as with application of high-temperature stress for 10 minutes.

(3) Southern Analysis

Genomic Southern analysis was carried out in order to determine the number of ZmDREB2A copies of the maize genome (FIG. 4). As in the case of Northern analysis, a C-terminal region of ZmDREB2A was used as a probe. In order to inspect the presence of highly homologous genes, membrane washing was carried out in 2 ways, i.e., under high stringency conditions and under low stringency conditions. Since only 1 band was observed via treatment under high stringency conditions, the number of maize ZmDREB2A copies is considered to be only 1. Under low stringency conditions, however, several bands were detected. This indicates the presence of several highly homologous genes.

3. Examination

*Arabidopsis thaliana* DREB2A is induced by dehydration, salt, or high-temperature stress. As with the case of DREB2A, expression of ZmDREB2A was frequently induced by salt or high-temperature stress (FIG. 2A). In contrast, expression thereof was not substantially induced by dehydration stress, and low-temperature-stress-induced expression thereof occurred at a considerably late time point. This expression pattern differs from that of DREB2A. When dehydration stress was applied to *Arabidopsis thaliana*, the expression level was continuously weak from 20 minutes to 2 hours after the stress application, the expression level became considerably strong 5 hours after the stress application, it reached the peak about 10 hours after the stress application, and the expression level 24 hours after the stress application was substantially the same as that 5 hours after the stress application (Liu et al., The Plant Cell 10, 1391-1406, 1998, Nakashima et al., Plant Molecular Biology 42, 657-65, 2000). In contrast, OsDREB2A expression in rice at the time of dehydration stress application was constantly, rather than transiently, somewhat strong (Dubouzet et al., described above). Although the expression pattern of ZmDREB2A is similar to that of rice, the expression level thereof is much weaker. *Arabidopsis thaliana* and rice were almost completely dehydrated 5 hours after application of dehydration stress; however, maize was not sufficiently dehydrated 5 hours after stress application. This indicates that maize is strongly resistant to dehydration stress. Although ZmDREB2A was responsive to dehydration, the conditions within 24 hours after the application of dehydration stress were not recognized to be sufficient. Accordingly, the expression thereof was not observed.

ZmDREB2A expression was induced mainly in the root. When the temperature was changed, however, expression was observed also in the leaf and in the stem. Salt stress was applied by soaking the underground portion of the plant in a sodium chloride solution, and dehydration stress was applied by removing the plant that had been subjected to hydroponic cultivation once from a stainless steel mesh. Such stress was applied more strongly to the underground portion. In the case of temperature stress, the leaf and the stem also receive such stress, and thus ZmDREB2A expression is induced in such portions. Although the expression level of ZmDREB2A is strong in the root, the expression thereof is observed throughout the entire plant, and expression is immediately induced upon reception of stress.

How the long-form and short-form mRNAs of ZmDREB2A were accumulated was inspected (FIG. 3). Expression of both types of mRNAs was induced by stress application; however, expression of short-form mRNA was more likely to be induced. Long-form mRNA has an intron, and a stop codon is present in the intron portion. Accordingly, protein synthesis is considered to be terminated. Thus, short-form mRNA is required when stress is applied. Also, greater amounts of short-form mRNAs, which are considered to be active forms (this will be examined in Example 3), were accumulated as the stress became stronger. The amount of short-form mRNAs is about 1/1,000 that of long-form mRNAs when no stress is imparted; however, the amount thereof is increased upon stress application (FIG. 3B). This suggests that active short-form mRNA is a gene that is necessary when the stress level is high. When low-temperature stress is imparted, accumulation of non-active long-form mRNAs is increased with the elapse of time, but accumulation of short-form mRNAs is not very significant. This indicates that activity of an enzyme required when short-form mRNA is formed from long-form mRNA is lowered by low-temperature stress (FIG. 3A).

Example 3

Examination of Transcription-Activating Mechanism Using Protoplast

1. Material and Method
(1) Cultured Cells

*Arabidopsis thaliana* cultured T87 cells were used. Cells stored in the BioResource Center of the Institute of Physical and Chemical Research were provided.

(2) Subculture Method and Medium

The compositions of growth medium (JPL medium) are as shown below. Culture and subculture were conducted at 22° C. with continuous application of a white light under mild agitation conditions. In the experiment, cells that had been subcultured for 5 to 6 days were used.

Stocks:

|  | Concentration (g/l) |
| --- | --- |
| Stock A |  |
| KNO$_3$ | 65.5 |
| CaCl$_2$•H$_2$O | 4.4 |
| MgSO$_4$•7H$_2$O | 3.7 |
| KH$_2$PO$_4$ | 1.7 |
| Stock B |  |
| H$_3$BO$_3$ | 6.2 |
| MnSO$_4$•4H$_2$O | 22.3 |
| ZnSO$_4$•7H$_2$O | 10.6 |
| KI | 0.83 |

-continued

| | Concentration (g/l) |
|---|---|
| Na$_2$MoO$_4$•2H$_2$O | 0.25 |
| CoCl$_2$•6H$_2$O | 0.025 |
| CuSO$_4$•5H$_2$O | 0.025 |
| Stock C | |
| FeSO$_4$•7H$_2$O | 2.78 |
| Na$_2$EDTA•2H$_2$O | 3.72 |
| Stock D | |
| Myo-inositol | 10 |
| Glycine | 0.2 |
| Stock VT | |
| Nicotinic acid | 0.5 |
| Pyridoxine-HCl | 0.5 |
| Thiamine-HCl | 0.4 |
| 100 mM Na$_2$HPO$_4$/KH$_2$PO$_4$ | |
| Na$_2$HPO$_4$•12H$_2$O | 71.62 |
| 0.2M KH$_2$PO$_4$ | 27.22 |

The above stock solutions and other reagents were mixed in the following manner to prepare the growth medium.

| | Per liter |
|---|---|
| Stock A | 30 ml |
| Stock B | 0.3 ml |
| Stock C | 2 ml |
| Stock D | 10 ml |
| Stock V.T. | 1 ml |
| Casamino acids | 0.1 g |
| Sucrose | 15 g |
| 100 mM Na$_2$HPO$_4$/KH$_2$PO$_4$ | 1 ml |
| 500 µM NAA | 2 ml |

(3) Preparation of Construct (Deletion Mutant)

pGreenIIE135Ω vector was used. A deletion mutant was prepared via two-phase PCR with the use of 2 pairs of primers (a pair of primer A and primer B and a pair of primer C and primer D) in accordance with a conventional technique. Primers were prepared from the portions to be deleted of a C-terminal deletion mutant and general PCR was carried out. pGreenII vector was treated with EcoRV and BamHI at 30° C. overnight, and a target fragment was inserted therein. The target fragment was amplified by PCR using primers, treated with EcoRV and BamHI at 30° C. overnight, and ligated using Ligation high (Toyobo). The plasmid was introduced into *E. coli* DH5α to obtain a kanamycin-tolerant strain. *E. coli* was transformed by the heat-shock method. The resultant was cultured in LB medium containing 25 mg/ml of kanamycin overnight to select a tolerant strain. The selected strain was subjected to plasmid extraction using an automated DNA separator (PI-100, Kurabo). Further, the resultant was treated with RNase at 37° C. for 1 hour, purified by phenol/chloroform extraction and ethanol precipitation, and then sequenced using a sequencer (ABI3100 Genetic Analyzer, Applied Biosystem Japan). The primers used are shown in Tables 2 to 4.

TABLE 2

| Deletion mutants | Names of primers | Sequences (5' → 3') |
|---|---|---|
| Long cDNA | AY108198-cDNA-BamH I | TTTGGATCCGGTCTATCGACTCC |
| | AY108198-Long-rev | AAAAGCAAGCACTCTTTTTA |
| Long ORF | AY108198-Long-BamH I | GGGGGATCCATGAAGGGAAAAGG |
| | AY108198-SmaI-rev | AAACCCGGGTCAGTTTAGCCGCTCC |
| Short cDNA | AY108198Short-BamH I | GGGGGATCCATGACGCTGGATCAGAA |
| | AY108198-Long-rev | AAAAGCAAGCACTCTTTTTA |
| Short ORF | AY108198Short-BamH I | GGGGGATCCATGACGCTGGATCAGAA |
| | AY108198-SmaI-rev | AAACCCGGGTCAGTTTAGCCGCTCC |

* From top to bottom, the primer sequences shown in Table 2 are those of SEQ ID NOs: 17 to 24 of the Sequence listing.

TABLE 3

| Deletion mutants | Names of primers | Sequences (5' → 3') |
|---|---|---|
| Forward primer | | |
| Common | AY108198 Short-BamH I | GGGGGATCCATGACGCTGGATCAGAA |
| Reverse primer | | |
| ZmDREB2A (1-272) | D2-short-del1 | GGGTCACTCATCAAGACACCAGGGC |
| ZmDREB2A (1-235) | D2-short-del2 | GGGTCATGGAAGATTTGTGATAGGCT |
| ZmDREB2A (1-208) | D2-short-del3 | GGGTCATCCAGCTGGGCATTTTGCC |
| ZmDREB2A (1-191) | D2-short-del4 | GGGTCAGTGTGAGGTGGATGGAT |
| ZmDREB2A (1-141) | D2-short-del5 | GGGTCAGGGGAAGTTAGTCCGTGC |
| ZmDREB2A (1-253) | del1.5 | GGGTCAGTGGATCGCTTTCCATCATCCT |

* From top to bottom, the primer sequences shown in Table 3 are those of SEQ ID NOs: 25 to 31 of the Sequence listing.

TABLE 4

| Deletion mutants | Names of primers | Sequences (5' → 3') |
|---|---|---|
| Primer A | | |
| Common | AY 108198 Short-BamHI | GGGGGATCCATGACGCTGGATCAGAA |

TABLE 4-continued

| Deletion mutants | Names of primers | Sequences (5' → 3') |
|---|---|---|
| Primers B, C | | |
| ZmDREB2A del141-191 | del-141-190-for | GCACGGACTAACTTCCCCAAGCCTGAAGCCTCTGAC |
| | del-141-190-rev | GTCAGAGGCTTCAGGCTTGGGGAAGTTAGTCCGTGC |
| ZmDREB2A del191-208 | del-191-208-for | CATCGCATCCACCTCACACTCATGTGGTATCCAAGAG |
| | del-191-208-rev | CTCTTGGATACCACATGAGTGTGAGGTGGATGCGATG |
| ZmDREB2A del208-235 | del-209-235-for | GGCAAAATGCCCAGCTGGGATGGTGGTGATGGTTTT |
| | del-209-235-rev | AAAACCATCACCACCATCCCAGCTGGGCATTTTGCC |
| ZmDREB2A del235-272 | del-236-272-for | CCTATCACAAATCTTCCACTGGATTCGAGTGTCTTG |
| | del-236-272-rev | CAAGACACTCGAATCCAGTGGGGGGAAGTTAGTCCG |
| ZmDREB2A del141-235 | del-141-235-for | CGGACTAACTTCCCCGATGGTGGTGATGGTTTT |
| | del-141-235-rev | AAAACCATCACCACCATCGGGGAAGTTAGTCCG |
| ZmDREB2A del141-272 | del-141-272-for | CGGACTAACTTCCCCCTGGATTCGAGTGTCTTG |
| | del-141-272-rev | CAAGACACTCGAATCCAGGGGGAAGTTAGTCCG |
| Primer D | | |
| Common | AY 108198-SmaI-rev | AAACCCGGGTCAGTTTAGCCGCTCC |

*From top to bottom, the primer sequences shown in Table 4 are those of SEQ ID NOs: 32 to 45 of the Sequence listing.

(4) Preparation of Plasmid and Introduction into Protoplast

Plasmid DNA was mass-produced in accordance with the alkali-SDS method using the Plasmid Mega kit or Maxi kit of Qiagen. A recombinant plasmid was precultured in 2 ml of LB medium containing antibiotics at 37° C. for 8 hours, transferred to 500 ml of LB medium (composition: 10 g of bacto-trypton, 5 g of bacto-yeast extract, 10 g of NaCl, and 1.5 ml of 1N NaOH per liter of medium), and further cultured overnight. The cultured cells were harvested, suspended in 50 ml of P1 solution, and then vigorously agitated. P2 solution (50 ml) was added thereto, the mixture was invertedly mixed, and the resultant was allowed to stand at room temperature for 5 minutes. P3 solution was added thereto, the mixture was agitated up and down, 50 ml of FWB solution was added, and the filtrate was removed. QBT buffer was added to the filtrate, the mixture was applied to the column, and plasmid DNA was eluted with the aid of QF buffer. The resultant was subjected to isopropanol precipitation, dissolved in an adequate amount of TE buffer, and the concentration was measured.

T87 cells that had been cultured for 5 to 6 days were recovered (5 g), the cells were suspended in 100 ml of an enzyme solution (0.4 M mannitol, 0.5 mM MES-KOH (pH 5.6), 0.1% Cellulase Onozauka R-10, 0.05% Macerozyme), and the suspension was treated while being agitated in the dark at 80 rpm for 2 hours to prepare protoplasts. The protoplasts were washed with Solution A (0.4 M mannitol, 0.5 mM MES-KOH (pH 5.6), 70 mM $CaCl_2$), and the protoplasts were then suspended in an MaMg solution (0.4 M mannitol, 15 mM $MgCl_2$, 0.5 mM MES-KOH (pH 5.6)) to a concentration of about $5.0 \times 10^6$ cells/ml. After 10 µg of reporter plasmid and effector plasmid were added, 100 µl of a PEG-CMS solution (400 mM mannitol, 100 mM $CaNO_3$, 40% PEG) was added thereto, the mixture was mildly agitated, and the resultant was then allowed to stand on ice for 30 minutes. The product was diluted with a diluent (0.4 M mannitol, 125 mM $CaCl_2$, 5 mM KCl, 5 mM glucose, 1.5 mM MES-KOH (pH 5.7)) and centrifuged to remove the supernatant. The protoplasts were suspended in MS-mannitol medium (0.4 M mannitol was added to MS medium from which sucrose had been removed), and the suspension was subjected to stationary culture at 22° C. in the dark for 20 hours.

The effector construct used in the experiment was prepared by ligating cDNA comprising full-length ZmDREB2A and a deletion mutation, the CaMV35S promoter, and the TMVΩ sequence. The reporter construct was prepared by ligating an alignment of 3 75-bp-fragments (DRE×3) containing DRE of the rd29A promoter, the TATA minimal promoter, and the GUS sequence. The internal standard plasmid was prepared by ligating the CaMV35S promoter and the luciferase gene. The effector, the reporter, and the internal standard plasmids were introduced into the protoplasts by the PEG method.

(5) Luciferase Activity Assay

Protoplasts were recovered by centrifugation at 500 rpm at room temperature for 5 minutes, the recovered protoplasts were suspended in 150 µl of crushing buffer (50 mM sodium-phosphate buffer, 1 mM EDTA, 0.1% Triton X-100, 10 mM β-mercaptoethanol), the suspension was crushed using a homogenizer, the product was centrifuged at 15,000 rpm at 4° C. for 10 minutes to remove insoluble fractions, and the resultant was designated as a cell extract. Luciferase activity was assayed using a Pickagene luciferase assay kit (Toyo Ink) in accordance with the manufacturer's instructions. The cell extract (10 µl) was allowed to react with 50 µl of Pickagene solution, and the activity was assayed using a luminometer.

(6) GUS Activity Assay

A substrate solution (100 µl, a mixture of a crushing buffer and 2.5 mM 4-MUG (4-methylumbilliferyl-β-D-glucuronide)) was mixed with 10 µl of cell extract, the mixture was allowed to react at 37° C. for 1 hour, and the product was added to 1 ml of reaction terminator (2M $Na_2CO_3$) to terminate the reaction. The resulting solution (100 µl) was used for the assay.

2. Results

Figure 5A:
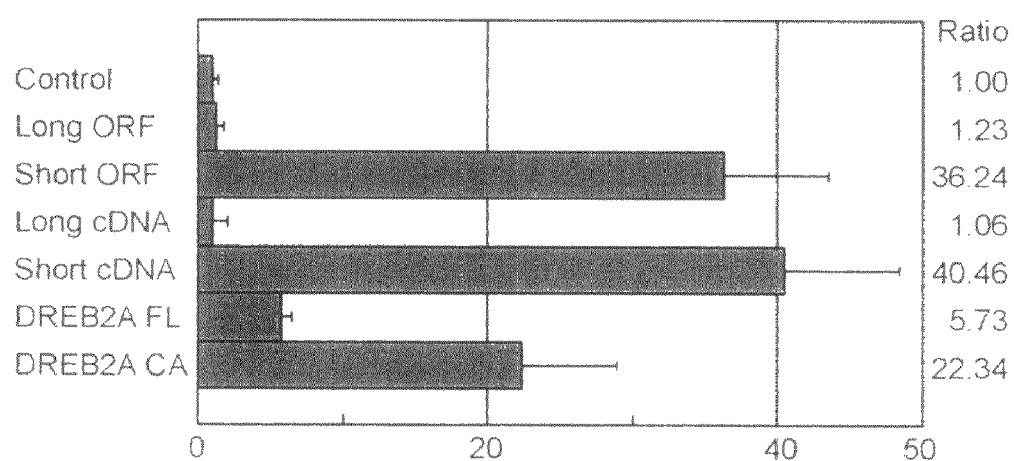
FIG. 5A shows the results of activity analysis of ZmDREB2A (protein activity of 2 embodiments of ZmDREB2A) using T87 protoplast. The experimental value is determined by dividing GUS activity by LUC activity, and the value attained with the use of a vector only is shown with 1 as a control: DREB2A FL: full-length DREB2A; DREB2A CA: modified DREB2A.
Figure 5B:
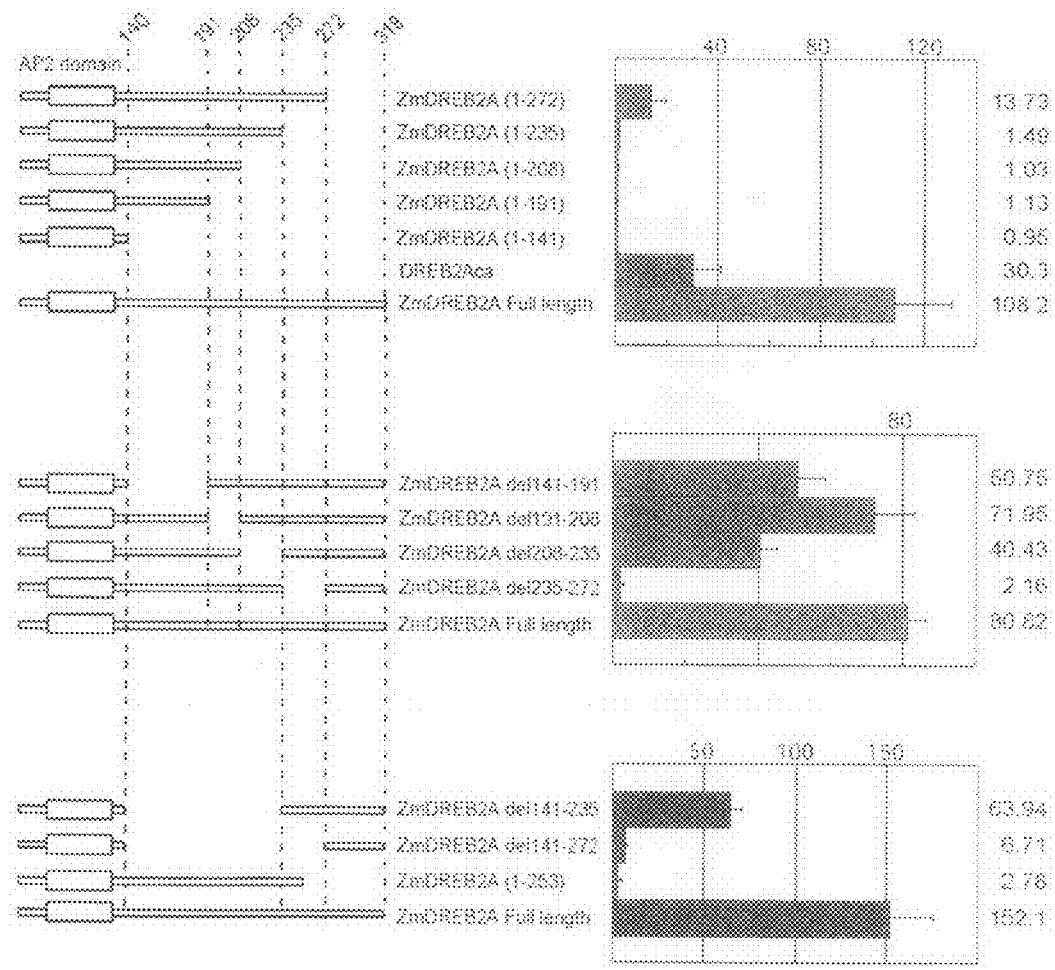
FIG. 5B shows the results of active domain analysis of ZmDREB2A (an internally-deleted variant of ZmDREB2A) using T87 protoplast. The experimental value is determined by dividing GUS activity by LUC activity, and the value attained with the use of an empty vector is shown with 1 as a control.

Full-length long-form cDNA, full-length short-form cDNA, a deduced ORF region extracted from long-form cDNA, and a deduced ORF region extracted from short-form cDNA were subjected to activity assay. ORF of long-form cDNA was prepared with reference to the portion of the sequence registered in the database (FIG. 1B, starting from methionine as an amino acid 72). Activation of GUS transcription was not substantially observed in both full-length long-form cDNA and ORF of long-form cDNA (FIG. 5A). In contrast, GUS/LUC activity was elevated 40 to 100 times in cells into which short-form cDNA had been introduced. The level of activity was about twice that of DREB2A of *Arabidopsis thaliana* (active form). In the experiment using cDNA comprising a deletion mutation added thereto, the activity level becomes considerably low with the deletion of a region from the C terminus to amino acid 272 (hereafter referred to as "272aa"). Further, with deletion of a region up to 236aa, substantially no activity was observed (FIG. 5B). Deleting the region from 235aa to 272aa, i.e., the internal region of a ZmDREB2A protein would result in an extremely low level of activity. Thus, a domain for activating ZmDREB2A transcription is considered to be present in the region between 235aa and the C-terminus.

3. Examination

In the transient expression system using T87 cell protoplasts, a high level of ZmDREB2A-inducible transcription activation was observed. This indicates that ZmDREB2A binds to DRE and functions as a transcription activator. Substantially no activity was observed in long-form cDNA; however, short-form cDNA was found to have a very high ability of transcription activation (FIG. 5A). In the case of long-form cDNA, a sequence of 53 nucleotides, which is present in the middle of a sequence, is deduced to be an intron, is absent in short-form cDNA, and causes a frame-shift. A stop codon is inserted in the sequence. This enables coding of an active protein. Long-form cDNA is registered as EST in the database, and methionine as 72aa is indicated as an initiation codon. When an ORF of such long-form cDNA is used as an effector, however, no transcription activation was observed.

When full-length cDNA was used as an effector, DREB2A of *Arabidopsis thaliana* exhibited low transcription activation ability; however, it exhibited high activity upon deletion of a region comprising 30 amino acids downstream of a DNA-binding domain (Sakuma et al., unpublished). On the contrary, ZmDREB2A exhibited high transcription activation ability in full-length cDNA, and activity levels did not significantly change even when an internal region (141aa to 208aa) was deleted (FIG. 5B). It is known that a large quantity of acidic amino acids is present at the C terminus and that a large quantity of acidic amino acids is present in transcription activating domains. Since transcription activity is significantly lowered upon deletion of the 236aa-272aa region at the C terminus, a transcription activating domain is deduced to be present in the vicinity thereof. As a result of searching for sequences around the 236aa-272aa region in the database, highly homologous sequences were found in wheat HvDRF1, rice OsDREB2B, and pearl millet DREB2A homologous proteins (FIG. 6). Since a region exhibiting higher activity than that of full-length cDNA was not observed upon deletion, it was deduced that a region equivalent to a DREB2A negative domain was not present.

No obvious differences were found between the phenotype of a plant into which DREB2A of *Arabidopsis thaliana* had been introduced and that of a wild type plant, and such transgenic plant is not tolerant to environmental stress. Thus, DREB2A protein was considered to be inactive with synthesis alone. This is because DREB2A comprises a serine (Ser)/threonine (Thr)-rich domain and phosphorylation of such domain may be necessary for activation (Liu et al., 1998). Also, DREB2A becomes active when a 135aa-165aa region of DREB2A is deleted (Sakuma et al., unpublished). The amino acid sequence of ZmDREB2A comprises a domain that is rich in Ser/Thr from 99aa to 118aa. ZmDREB2A is always active because of the presence of a conformational mechanism by which the aforementioned domain is likely to be phosphorylated.

A PEST sequence is present in a 135aa-165aa region of DREB2A. This sequence refers to a domain that is a 10-bp-or-longer sequence partitioned by basic amino acids and is rich in proline (P), glutamic acid (E), serine (S), threonine (T), and aspartic acid (D). This domain is contained in many short-life proteins, recognized by enzymes, and decomposed. The presence of the PEST sequence in DREB2A and in ZmDREB2A was inspected via WWW PEST-find analysis at EMBNet AUSTRIA No resulting candidate sequence for ZmDREB2A was discovered. This indicates that DREB2A is decomposed by the PEST sequence and thus does not generally exhibit activity. It is also reported that OsDREB2A does not exhibit transcription activity (Dubouzet et al., The Plant Journal, 33, 751-763). This OsDREB2A was also inspected concerning the presence of the PEST sequence, and there was no domain equivalent thereto. Thus, it is unlikely that such sequence is the only reason for inactivation.

Example 4

Analysis of ZmDREB2A Function Using a Transformant (1)

In order to precisely inspect functions of ZmDREB2A in plants, ZmDREB2A was introduced into *Arabidopsis thaliana* to prepare transgenic *Arabidopsis thaliana*, and tolerance to low-temperature and dehydration stresses of a target gene or a transgenic plant was analyzed.

1. Material and Method
(1) Sample Plant and Growth Conditions

Full-length ZmDREB2A was introduced into plants to produce transgenic plants. Dehydrated seeds were soaked in a solution of 1% NaClO and 0.02% Triton X-100 for 10 minutes for sterilization. The sterilized seeds were sowed on GMK agar medium, subjected to low-temperature treatment at 4° C. for 2 days, and then grown at 22° C. with a photoperiod of 16 hours for 14 days. Plants (4 plants) were recovered, and the expression level of ZmDREB2A therein was analyzed. Further, the remaining plants were transferred to pots, allowed to grow for 1 week, and then subjected to stress tolerance tests or the like. Round plant pots containing professional soil (Kakiuchi) were used.

(2) Growth Medium

The compositions of the plant media are as shown below.

GMK agar medium: Murashige-Skoog salt (Wako Pure Chemicals), 0.4 g/l Tiaine-HCl, 0.1 g/l myo-inositol, 3% (w/v) sucrose, 1 nM indol acetic acid, 10 nM 6-benzyl amino purine, 0.83% bacto-agar, and 30 mg/l kanamycin GMKV agar medium: GMK agar medium, 100 mg/l vancomycin (3) Preparation of Transgenic *Arabidopsis thaliana*

*Arabidopsis thaliana* was transformed using pgreen E12 35SΩ-ZmDREB2A short form used in the experiment involving the use of protoplasts. Plasmids (1 µl, about 70 µg) were mixed with 40 µl of competent cells for electroporation (*Agrobacterium* GV3101 into which helper plasmid pSoup had been introduced in advance), the resultant was introduced into a cuvette that had been cooled to 4° C., and electroporation was carried out at 200Ω, 25 µF, and 2.5 kV. SOC medium (1 ml, 20 g of bacto-tryptone, 5 g of bacto-yeast extract, 0.5 g of NaCl, 0.02M glucose, 0.01M $MgSO_4$, 0.01M $MgCl_2$) was added, culture was conducted at 28° C. for 1 hour, and culture was further conducted in LB agar medium containing kanamycin for 2 days to select tolerant strains.

*Arabidopsis thaliana* was infected with the transgenic *Agrobacterium* in accordance with a conventional technique.

Seeds obtained from infected *Arabidopsis thaliana* were sowed on GMKV medium, and grown kanamycin-tolerant plants were selected. The selected plants were transferred to a fresh GMKV medium and transplanted to soil when they had adequately grown.

(4) Northern Analysis and Quantitative RT-PCR Analysis

Northern analysis and quantitative RT-PCR analysis were carried out in accordance with Example 2, except that the amount of RNA used was 5 µg.

(5) Stress Application

In order to inspect the expression levels of ZmDREB2A and stress-inducible gene rd29A influenced by low-temperature and dehydration stress, 4 cell lines into which ZmDREB2A had been introduced, a cell line into which DREB1A and DREB2A (a wild type and an active form) had been introduced, and a cell line into which a pBI121 vector control had been introduced were subjected to low-temperature, dehydration, and salt stress application. Low-temperature stress was applied by allowing the plate to stand at 4° C. for 5 hours. Dehydration stress was applied by pulling *Arabidopsis thaliana* out of the medium while leaving no medium on the root, placing the same on the plate, and treating the same in a clean bench for 5 hours. Salt stress was applied by pulling *Arabidopsis thaliana* out of the medium while leaving no medium on the root and soaking the same in a 250 mM NaCl solution.

(6) Stress Tolerance Test

Freezing stress tolerance was evaluated by growing plants in GMK medium for 21 days, transferring the plants to soil pots, growing the plants for 1 week, transferring the plants to an incubator at −6° C. to treat the plants for 30 hours, and growing the plants for 1 week, followed by evaluation.

Dehydration stress was applied by sowing plants on medium, growing the plants for 21 days, transferring the plants to soil pots, growing the plants for 1 week, terminating watering, and then watering again about 10 days thereafter. Recovery conditions of the plants thereafter were observed to evaluate the tolerance.

(7) Analysis of Inducible Gene Using Microarray

An experiment was carried out using the *Arabidopsis* 2 oligo DNA microarray kit (21,500 genes spotted, Agilent). Reagents and apparatuses used in the experiment were those of Agilent unless otherwise specified.

In the same manner as in Example 2, RNA was extracted via the Trizol method (Invitrogen). Four plants were used per sample. The extracted RNA was inspected using the Bioanalyzer to confirm that the rRNA bands were clear and that rRNA ratios were consistent with theoretical ratios.

Total RNA (800 ng) was used for each sample, 400 ng thereof was labeled with Cy3, and the other 400 ng was labeled with Cy5. T7 promoter primers were added thereto, and the products were subjected to thermal denaturation at 65° C. for 10 minutes, followed by quenching in ice for 5 minutes. The cDNA synthesis master mix (2.0 µl of 5× First Strand buffer, 1.0 µl of 0.1M DTT, 0.5 µl of 10 mM dNTP mix, 0.5 µl of MMLV-RT, and 0.25 µl of RNaseOUT) was added thereto, and the resultant was treated at 40° C. for 2 hours. Thereafter, the reaction product was treated at 65° C. for 15 minutes, and the reaction was terminated, followed by quenching in ice for 5 minutes. To the reaction solutions, 1.2 µl of 10 mM cyanine 3-CTP (cytosine triphosphate) and 1.2 µl of 10 mM cyanine 5-CTP were added, the transcription mix (7.65 µl of nuclease-free water, 10.0 µl of 4× transcription buffer, 3.0 µl of 0.1M DTT, 4.0 µl of NTP mix, 3.2 µl of 50% PEG (pre-warm, 40° C.), 0.25 µl of RNaseOUT, 0.3 µl of inorganic pyrophosphatase, and 0.4 µl of T7 RNA polymerase) was added thereto, and the mixtures were vigorously agitated to proceed with the reaction under shaded conditions at 40° C. for 120 minutes. To the product, 60 µl of nuclease free water, 350 µl of RLT-buffer, and 250 µl of EtOH were added and mixed using a pipette. The resulting solution was transferred to a RNeasy mini column (Qiagen) equipped with a 2-ml collection tube and then centrifuged at 13,000 rpm for 30 seconds. The column was transferred to a new collection tube, 500 µl of RPR-buffer was added thereto, and centrifugation was carried out at 13,000 rpm for 30 seconds. This procedure was repeated once, the column was transferred to a 1.5-ml collection tube, 30 µl of RNase-free water was added thereto, the tube was allowed to stand for 1 minute, and centrifugation was carried out at 13,000 rpm for 30 seconds to recover cRNA. This procedure was performed again, and absorbance at 260 nm was assayed to determine the concentration.

cRNA target solution (1 µg of Cy3-labeled cRNA, 1 µg of Cy5-labeled cRNA, 50 µl of 10× control target, and up to 250 µl of nuclease free water) was prepared, 10 µl of 25× fragmentation buffer was added thereto, and the mixture was vigorously agitated to fragmentize the target. The solution was treated under shaded conditions at 60° C. for 30 minutes. 2× hybridization buffer (250 µl) was added thereto, the mixture was agitated without foaming, and the resultant was transferred to microarray slides. Hybridization was then carried out at 60° C. for about 17 hours. The slides after hybridization were washed with washing buffer 1 (6×SSC, 0.005% Triton X-102) at room temperature for 10 minutes. Subsequently, the slides were washed with a washing buffer 2 (0.1×SSC, 0.005% Triton X-102) at 4° C. for 5 minutes. The washed slides were dried by nitrogen gas with the aid of a filter air gun. In the end, the slides were set on the Agilent microarray scanner slide holder for scanning, and spot digitalization and data analysis were carried out.

Figure 7:
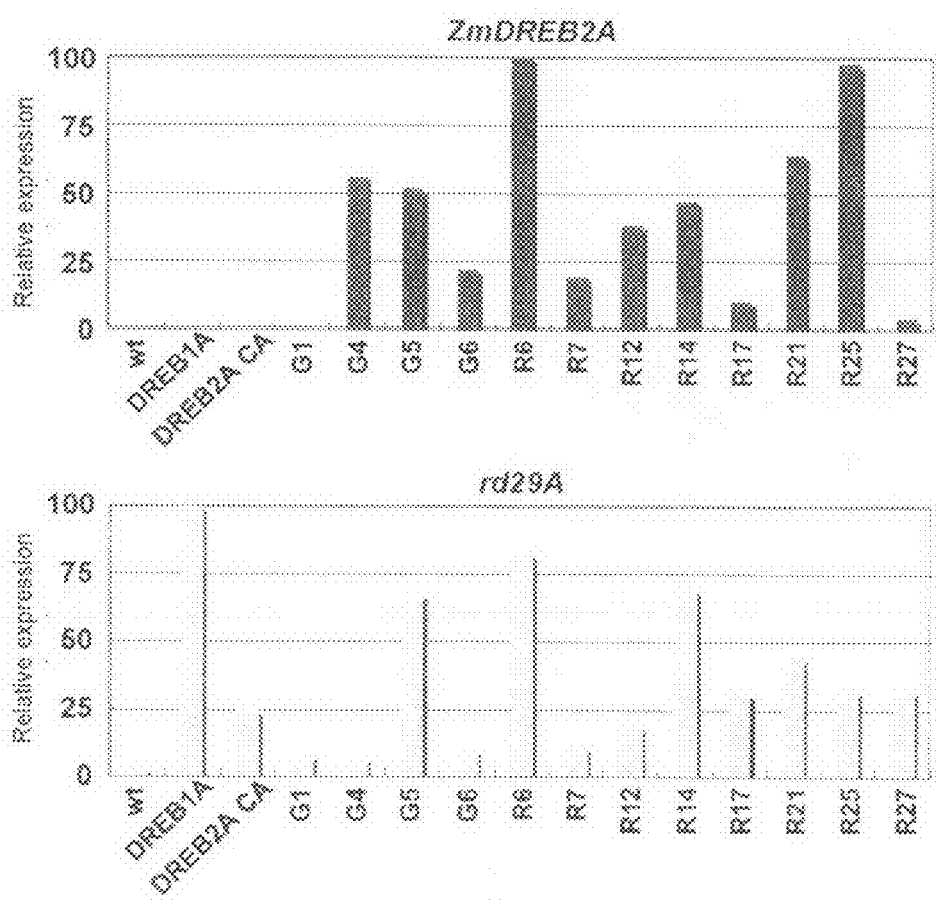
FIG. 7 shows the expression levels of ZmDREB2A and rd29A in ZmDREB2A-overexpressing *Arabidopsis thaliana*.

2. Results (1) Analysis of Traits of ZmDREB2A Transgenic *Arabidopsis thaliana* and Expression of Introduced Gene 51 ZmDREB2A transgenic lines were obtained, and 32 lines thereof that yielded T2 seeds in amounts sufficient for subsequent analyses were subjected to quantitative RT-PCR to analyze the expression levels of introduced genes. Partial results are shown in FIG. 7. The plants were grown in GMK agar medium and conditions thereof 21 days after sowing were observed (the top row, FIG. 8A). Compared with control lines, the overexpressing plants were found to be likely to experience dwarfing. Plants were grown in GMK medium for 2 weeks and then transferred to soil, and conditions thereof were observed. FIG. 8A shows the plants on day 35 (i.e., 21 days after transplantation). As with the case involving the use of an agar plate, such plants showed retardation of growth. The target gene that is controlled by ZmDREB2A in *Arabidopsis thaliana* is unknown; however, ZmDREB2A induced expression of a reporter gene bound to a site downstream of a DRE sequence of an rd29A promoter in Example 3. It is accordingly deduced that the expression levels of the rd29A gene would be elevated in ZmDREB2A-overexpressing *Arabidopsis thaliana*. FIG. 8B shows the results of Northern analysis of the introduced genes and rd29A genes in ZmDREB2A-overexpressing *Arabidopsis thaliana*. Four transgenic lines in which the expression levels of the introduced genes and of rd29A genes were high and changes in traits were observed (i.e., R6, R14, R21, and R25) were subjected to subsequent analysis.

(2) Evaluation of Stress Tolerance of ZmDREB2A-Transgenic *Arabidopsis thaliana*

Figure 9:
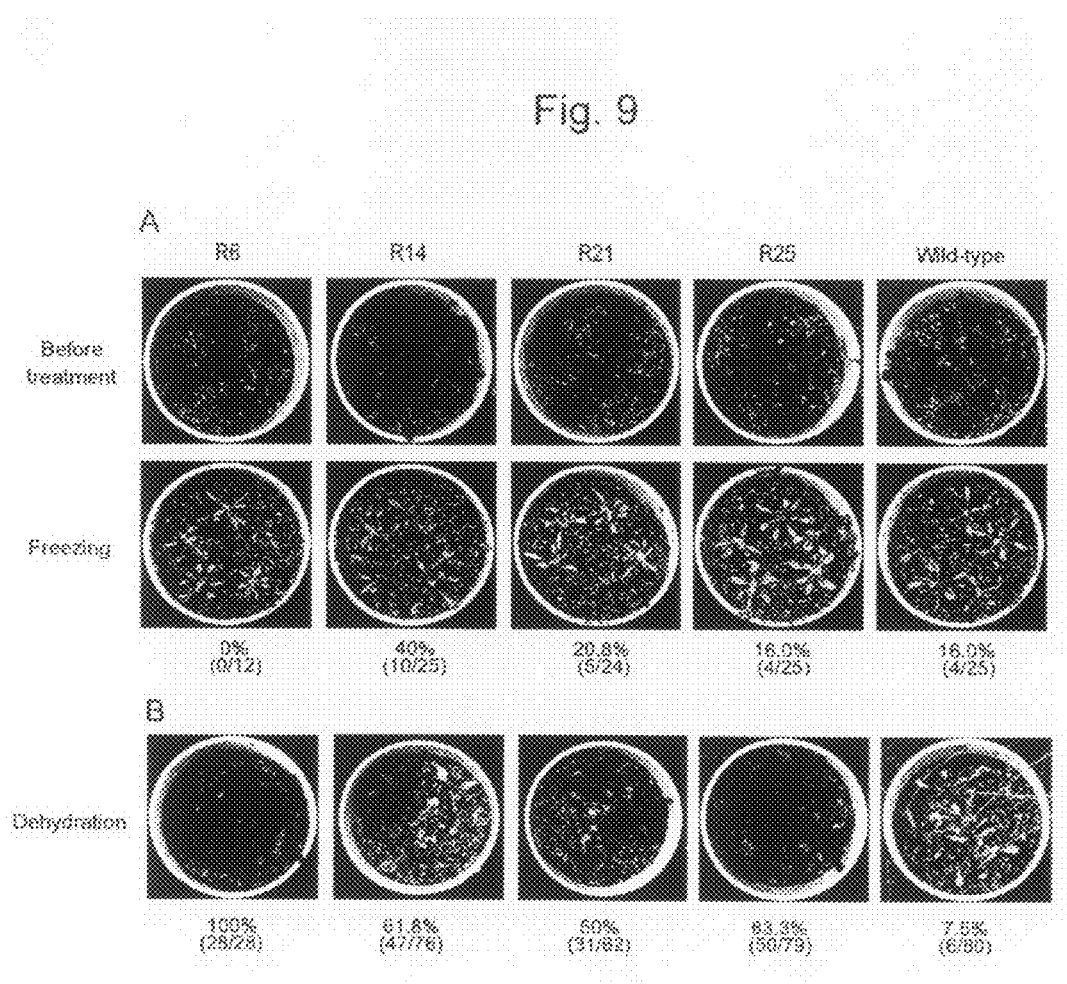
FIG. 9 shows the results of a stress tolerance test of ZmDREB2A-overexpressing *Arabidopsis thaliana*. (A) Freezing tolerance: upper portion: the control; lower portion: after freezing treatment; (B) dehydration tolerance: numerical values in parentheses indicate the ratios of viable counts/number of samples.

The four transgenic *Arabidopsis thaliana* lines selected above were evaluated in terms of tolerance upon freezing and dehydration stress application. A vector-introduced line (pBI121 control) was designated as a control line. Freezing tolerance was tested twice, and dehydration tolerance was tested 4 times. When freezing stress was applied, 10 among the 25 R14 plants survived; however, all other transgenic plants died (FIG. 9A). Dehydration stress was applied by transferring the plants on day 21 to soil pots, growing the plants under general conditions for 1 week, and terminating watering for 10 days. Thereafter, traits were observed for 1 to 2 weeks to evaluate the tolerance. R6 exhibited particular improvement in tolerance. The other 3 lines exhibited relatively high tolerance compared with the control plants (FIG. 9B). Thus, ZmDREB2A-overexpressing *Arabidopsis thaliana* exhibited dehydration tolerance; however, it exhibited substantially no improvement in freezing stress tolerance.

(3) Analysis of Target Gene Using Microarrays

In order to identify genes with expression levels that vary upon overexpression of ZmDREB2A, extensive expression analysis was conducted using an Agilent *Arabidopsis* 2 oligo DNA microarray kit (Table 5). Microarray analysis involved the use of R6 and R14 lines. The R6 line exhibits stronger expression of introduced genes. These lines were subjected to experimentation twice, and the correlation coefficients of two experimentations were very high. The number of genes that had exhibited expression levels that were 5 times or higher than those of the controls in one of the experimentations was 88. These genes were classified in terms of functions, and 11 genes were LEA protein-related genes, 7 genes were heat shock protein-related genes, 5 genes were oxidative stress related genes, 7 genes were oleosin-related genes, 5 genes were sugar metabolism related genes, 2 genes were membrane transport-related genes, and 6 genes were budding-related genes.

TABLE 5

Genes with expression levels that were found to be increased via microarray analysis in ZmDREB2A-overexpressing plants

| Gene function | Accession No. | Ratio R6 | Ratio R14 | DRE | Induction DREB2A | Induction Stress |
|---|---|---|---|---|---|---|
| LEA protein | | | | | | |
| late embryogenesis abundant M10 protein | AT2G41280 | 5.9 | 6.9 | — | — | — |
| late embryogenesis abundant protein-like | AT3G53040 | 21.0 | 25.0 | 1 | — | — |
| late embryogenesis abundant protein (AtECP63) | AT2G36640 | 15.9 | 23.7 | — | — | — |
| late embryogenesis abundant protein LEA like | AT5G06760 | 7.2 | 9.7 | 1 | — | D |
| late embryogenesis-abundant protein, putative | AT1G52690 | 19.5 | 25.8 | 1 | 23.2 | N, D |
| late-embryogenesis abundant protein, putative | AT1G32560 | 5.9 | 8.5 | 1 | — | N |
| low-temperature-induced 65 kD protein | AT5G52300 | 4.9 | 5.6 | 1 | 6.1 | N |
| low-temperature-induced protein 78 (rd29A) | AT5G52310 | 5.4 | 4.6 | 3 | 11.9 | N, D, C |
| LEA76 homologue type2 | AT3G15670 | 16.8 | 21.4 | 3 | — | N |
| similar to late embryogenesis abundant proteins | AT2G35300 | 7.6 | 9.6 | — | — | — |
| similar to late embryogenesis abundant proteins | AT2G23110 | 8.2 | 7.9 | — | — | — |
| Heat shock | | | | | | |
| heat shock protein 22.0 | AT4G10250 | 8.4 | 5.2 | — | 6.1 | H |
| heat shock protein 70 | AT3G12580 | 10.2 | 4.3 | 1 | 9.1 | N, H |
| heat shock transcription factor-like protein | AT5G03720 | 17.6 | 10.5 | 2 | 41.2 | N, H |
| 17.6 kDa heat shock protein (AA 1-156) | AT1G53540 | 6.7 | 4.2 | 1 | 6.1 | H |
| 70 kD heat shock protein | AT2G32120 | 6.7 | 4.4 | 1 | 3.6 | H |
| AtHSP23.6-mito | AT4G25200 | 13.0 | 12.7 | — | — | H |
| chloroplast-localized small HSP, putative | AT1G52560 | 18.6 | 18.1 | * | 14.0 | H |
| detoxification | | | | | | |
| glutathione transferase, putative | AT2G29460 | 6.7 | 4.7 | 1 | — | — |
| peroxidase, putative | AT1G49570 | 19.6 | 7.5 | — | 5.4 | — |
| peroxidase, putative | AT5G19890 | 15.7 | 4.8 | — | 5.9 | — |
| peroxiredoxin | AT1G48130 | 7.1 | 8.1 | — | — | — |
| ascorbate peroxidase (APX) | AT3G09640 | 9.3 | 6.8 | * | 8 | H |
| oil body localization | | | | | | |
| oleosin | AT5G40420 | 26.9 | 25.0 | — | — | — |
| oleosin | AT3G01570 | 8.9 | 16.2 | — | — | — |
| oleosin | AT3G27660 | 18.0 | 13.6 | — | 10.3 | — |
| oleosin | AT2G25890 | 8.2 | 11.1 | — | — | — |
| oleosin | AT4G25140 | 5.8 | 7.3 | — | — | — |
| 11-beta-hydroxysteroid dehydrogenase-like | AT5G50600 | 4.8 | 7.9 | — | — | — |
| embryo-specific protein 1 (ATS1) | AT5G55240 | 4.0 | 7.3 | 1 | — | — |
| Glucose metabolism | | | | | | |
| glycosyltransferase family | AT4G27560 | 6.9 | 4.4 | 3 | 19.0 | C |
| monosaccharide transporter, putative | AT1G34580 | 8.8 | 6.4 | 3 | 4.1 | — |
| putative galactinol synthase | AT1G09350 | 22.4 | 13.7 | 3 | 27.8 | C |
| putative glucose acyltransferase | AT3G10450 | 9.4 | 5.7 | * | 9.8 | — |
| putative monogalactosyldiacylglycerol synthase | AT2G11810 | 14.0 | 3.7 | * | — | — |
| Membrane traffick | | | | | | |
| putative peptide transporter | AT1G69870 | 6.1 | 4.4 | 1 | 11.8 | N, C |
| cyclic nucleotide-regulated ion channel | AT1G01340 | 5.5 | 4.2 | * | 5.3 | — |

TABLE 5-continued

Genes with expression levels that were found to be increased via microarray analysis in ZmDREB2A-overexpressing plants

| | | Ratio | | | Induction | |
|---|---|---|---|---|---|---|
| Gene function | Accession No. | R6 | R14 | DRE | DREB2A | Stress |
| Seed maturation | | | | | | |
| germin-like protein | AT5G39150 | 7.8 | 8.6 | * | 6.2 | — |
| germin-like protein | AT5G39180 | 6.4 | 6.7 | * | 4.7 | — |
| putative seed maturation protein | AT2G42560 | 15.1 | 19.8 | 2 | — | — |
| pathogenesis | | | | | | |
| pathogenesis-related protein 1 precursor, 19.3K | AT4G33720 | 4.9 | 7.0 | — | 21.6 | — |
| Other functions | | | | | | |
| ABA-regulated gene (ATEM6) | AT2G40170 | 11.0 | 18.1 | — | — | — |
| ABA-responsive element binding protein, putative | AT2G36270 | 5.4 | 7.2 | — | — | — |
| acid phosphatase type 5 | AT3G17790 | 10.9 | 4.4 | — | 1.9 | N |
| AIG1 | AT1G33960 | 6.2 | 4.7 | — | — | — |
| AtHVA22b-like protein | AT5G62490 | 5.9 | 5.9 | — | — | — |
| BCS1 protein-like protein | AT3G50940 | 9.9 | 4.9 | 1 | 7.2 | — |
| cinnamyl-alcohol dehydrogenase ELI3-2 | AT4G37990 | 44.3 | 50.6 | 2 | 4.7 | N |
| cysteine proteinase | AT4G36880 | 27.1 | 19.5 | 1 | 10.8 | — |
| cysteine proteinase | AT3G54940 | 6.3 | 8.6 | — | — | — |
| cytochrome p450 family | AT4G13290 | 7.0 | 5.7 | * | — | — |
| expressed protein | AT3G02480 | 47.9 | 44.5 | 2 | 12.4 | N, D |
| expressed protein | AT3G02040 | 21.6 | 6.5 | — | — | — |
| expressed protein | AT1G05340 | 6.5 | 5.9 | 1 | 6.5 | N |
| expressed protein | AT1G75750 | 8.3 | 4.4 | 2 | 5.5 | H |
| expressed protein | AT2G21180 | 6.1 | 4.1 | 2 | 9.3 | — |
| expressed protein | AT2G32190 | 5.0 | 4.0 | — | 5 | — |
| hypothetical protein | AT1G17710 | 36.7 | 16.1 | | 3.5 | — |
| hypothetical protein | AT1G05510 | 5.1 | 10.3 | — | — | — |
| hypothetical protein | AT1G23070 | 6.1 | 9.7 | * | — | — |
| hypothetical protein | AT1G65090 | 5.6 | 8.6 | — | — | — |
| hypothetical protein | AT1G73120 | 4.7 | 8.2 | — | — | — |
| hypothetical protein | AT3G24340 | 12.7 | 6.4 | * | — | — |
| hypothetical protein | AT1G01470 | 10.2 | 6.4 | 3 | 13.2 | N, D, C |
| malate synthase-like protein | AT5G03860 | 17.9 | 18.0 | — | 2 | — |
| phosphoinositide specific phospholipase C, putative | AT3G55940 | 10.4 | 6.3 | * | 15.4 | — |
| putative desiccation related protein | AT2G46140 | 7.9 | 5.0 | 1 | 8.1 | N, D |
| putative glutamyl tRNA reductase | AT2G31250 | 11.5 | 7.3 | * | — | — |
| putative isocitrate lyase | AT3G21720 | 12.3 | 11.5 | 1 | — | — |
| putative nonspecific lipid-transfer protein | AT2G38530 | 11.1 | 6.8 | 2 | 8.8 | — |
| putative protein | AT4G25580 | 14.9 | 20.6 | 2 | — | N |
| putative protein | AT4G21020 | 18.2 | 20.4 | 2 | 13.5 | — |
| putative protein | AT5G01300 | 9.5 | 14.5 | — | — | — |
| putative protein | AT5G20790 | 21.2 | 9.7 | * | 2.8 | — |
| putative protein | AT5G23220 | 15.4 | 8.4 | 1 | 7.9 | — |
| putative protein | AT4G25850 | 7.4 | 8.4 | 2 | — | — |
| putative protein | AT4G39130 | 4.7 | 6.1 | * | — | — |
| putative protein | AT5G64080 | 9.6 | 6.0 | 1 | 6 | — |
| putative protein | AT4G34300 | 6.8 | 5.1 | * | — | — |
| ribonuclease, RNS1 | AT2G02990 | 9.2 | 4.2 | 1 | — | — |
| serine carboxypeptidase II, putative | AT1G43780 | 9.5 | 6.7 | * | — | — |
| serine carboxypeptidase, putative | AT1G33540 | 19.7 | 8.7 | * | 16.8 | — |
| unknown protein | AT3G17520 | 36.9 | 41.6 | — | 16.8 | N, D |
| unknown protein | AT1G08310 | 13.0 | 6.0 | * | — | — |
| unknown protein | AT1G23110 | 17.3 | 5.6 | * | — | — |

Ratios: Signal intensities of normalized wild-type plants and normalized overexpressing plants were determined, two hybridization values were averaged, and the resulting values were averaged.

DRE: The database of full-length cDNA of *Arabidopsis thaliana* (Riken) was used for reference. "DRE" represents the number of a DRE sequence (ACCGAC) that is present within 1,000 nucleotides upstream of the transcription initiation point.

*: Genes with full-length cDNA is not registered at RARGE.

DREB2A: Genes with expression levels that are increased (at least 3 times) when modified DREB2A is applied to the array. Numerical values indicate the ratios attained at that time.

Stress: Genes with expression levels that increased at least 3 times upon stress application. (N: 250 mM NaCl for 10 hours; D: dehydration for 10 hours; C: 4° C. for 10 hours; H: high-temperature for 5 hours)

3. Discussion

*Arabidopsis thaliana*-overexpressing plants (32 lines) were allowed to grow for 2 weeks and then subjected to inspection of the ZmDREB2A expression levels (FIG. 8B). As a result, the expression levels of ZmDREB2A were found to be high in plants exhibiting retardation of growth. From among these lines, 4 lines exhibiting high ZmDREB2A expression levels were selected. The R6 line exhibited the highest ZmDREB2A expression level among the selected lines, although the R6 line exhibited a low germination rate.

Compared with wild-type plants, these 4 transgenic plants were slow to grow (FIG. 8A). It has already been reported that plants in which DREB/CBF type genes were overexpressed with the use of 35S promoter are slow to grow. However, what has been reported in the past was the DREB1 type gene, and phenotype differences have not been observed in DREB2A- or rice-OsDREB2A-overexpressing *Arabidopsis thaliana*. Since growth retardation occurred in DREB2A-type genes here, ZmDREB2A is considered to have a transcription activating ability in plants without modification, unlike *Arabidopsis thaliana* DREB2A or rice OsDREB2A.

Expression of DREB2A functions is considered to require some post-translational modifications. Sakuma et al. prepared active DREB2A and subjected active DREB2A transgenic *Arabidopsis thaliana* to microarray analysis (unpublished). As a result of microarray analysis of ZmDREB2A-overexpressing *Arabidopsis thaliana*, many common genes with DREB2A downstream genes and NaCl-inducible genes were detected (Table 5). A promoter sequence comprising a region up to 1,000 bp upstream from the transcription initiation point, which is disclosed in the database of *Arabidopsis thaliana* full-length cDNA (Riken) (http://rarge.gsc.riken.go.jp/), and 35 genes among the identified genes were consequently found to comprise a DRE sequence. Among these 35 genes, expression levels of 24 modified DREB2A genes were found to be increased. ZmDREB2A is considered to bind to a DRE sequence and induce expression of a downstream gene. Accordingly, increased expression levels of genes having such promoter sequences are considered to be induced directly by ZmDREB2A proteins. Thus, ZmDREB2A is considered to function in a manner similar to that of DREB2A in *Arabidopsis thaliana*, and ZmDREB2A was identified to be a DREB2 type gene.

Example 5

Analysis of ZmDREB2A Functions Using Transformant (2)

In order to thoroughly inspect the functions of ZmDREB2A in plants, ZmDREB2A was introduced into *Arabidopsis thaliana* in accordance with the procedure of Example 4 to prepare transgenic *Arabidopsis thaliana*, and high-temperature stress tolerance of target genes and transgenic plants was analyzed.

Materials and methods employed were basically in accordance with those of Example 4. Two plants each of two ZmDREB-overexpressing *Arabidopsis thaliana* lines (i.e., line 6 and line 25) were used. Seedlings that had been grown on GM medium for 18 days were transferred to pots containing culture soil. After the plants were grown for 11 days, the terrestrial parts were soaked in a water bath at 44° C. for 10 minutes (i.e., high-temperature stress application). The plants were cultured under common conditions thereafter, and growth conditions were observed 4 days and 7 days later. The results are shown in FIG. 10.

Control plants died 7 days after stress application; however, one of the line 6 plants survived (FIG. 10). Thus, ZmDREB2A was found to contribute to high-temperature stress response.

Example 6

Analysis of ZmDREB2A Functions Using Transformant (3)

(1) Viability Against High-Temperature Stress

Plants into which ZmDREB2A had been introduced were sowed on kanamycin-containing GM agar medium, the plants were cultured for 6 days, and the cultured plants were transferred on a filter paper soaked in 4 ml of GM medium (in a petri dish). The plants were first grown at 22° C. for 2 days, allowed to stand at 22° C., 44° C., or 45° C. (i.e., high-temperature stress) for 1 hour, and then returned to 22° C. to grow. As a control, *Arabidopsis thaliana* into which ZmDREB2A was not introduced (i.e., a wild type) was allowed to grow in the same manner.

Figure 11:
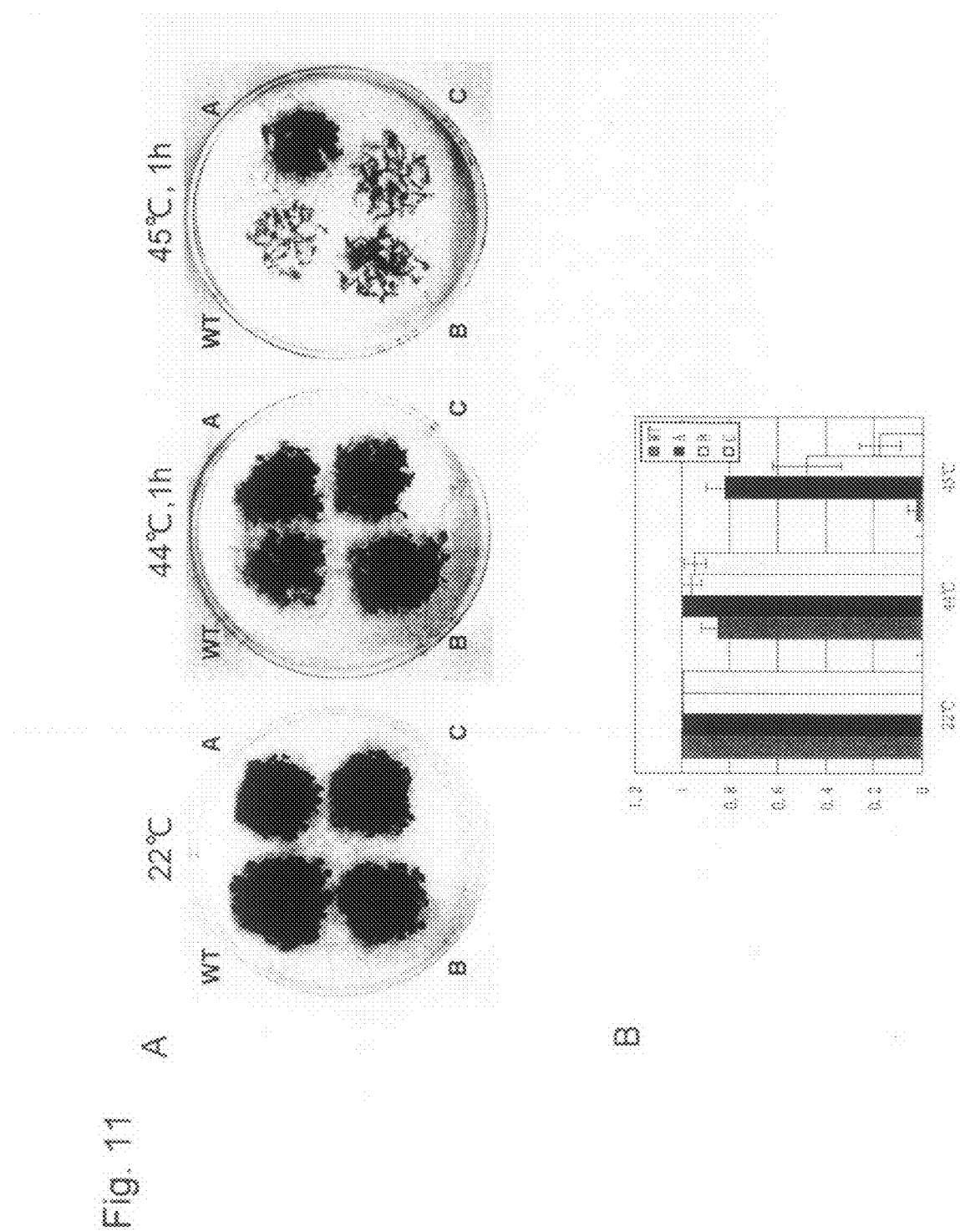
FIG. 11 shows plants to which high-temperature stress has been applied and the survival ratio thereof (mean and standard deviation (n≧50)). In the drawing, WT indicates a control plant into which ZmDREB2A has not been introduced. A, B, and C each indicate a plant into which ZmDREB2A has been introduced (3 lines).

FIG. 11 shows plants that had been grown in liquid GM medium for an additional 2 weeks after the test and the viability thereof (the mean and the standard deviation ($n \geq 50$)). "WT" represents a control plant into which ZmDREB2A has not been introduced, and A, B, and C each represent a plant into which ZmDREB2A has been introduced (3 lines in total).

As is apparent from FIG. 11, a plant into which ZmDREB2A has been introduced exhibited significantly higher high-temperature stress tolerance than a wild type plant.

(2) Northern Analysis

Plants into which ZmDREB2A has been introduced were subjected to common growth conditions, high-temperature stress (at 37° C. for 1 hour or 5 hours), salt stress (in 250 mM saline for 5 hours), or dehydration stress (dehydrated for 5 hours), and expression of genes, i.e., At5g03720 (AtHSFA3), At3g12580 (heat shock protein 70), At1g52560 (chloroplast-localized small heat shock protein), At4g25200 (AtHSP23.6-mito), At4g10250 (heat shock protein 22.0), and At5g12030 (heat shock protein 17.6A), regarding which expressions is known to be induced particularly by high-temperature stress, was analyzed via the Northern method. As a control, *Arabidopsis thaliana* into which ZmDREB2A was not introduced (i.e., a wild type (WT)) was allowed to grow in the same manner and then analyzed.

Figure 12:
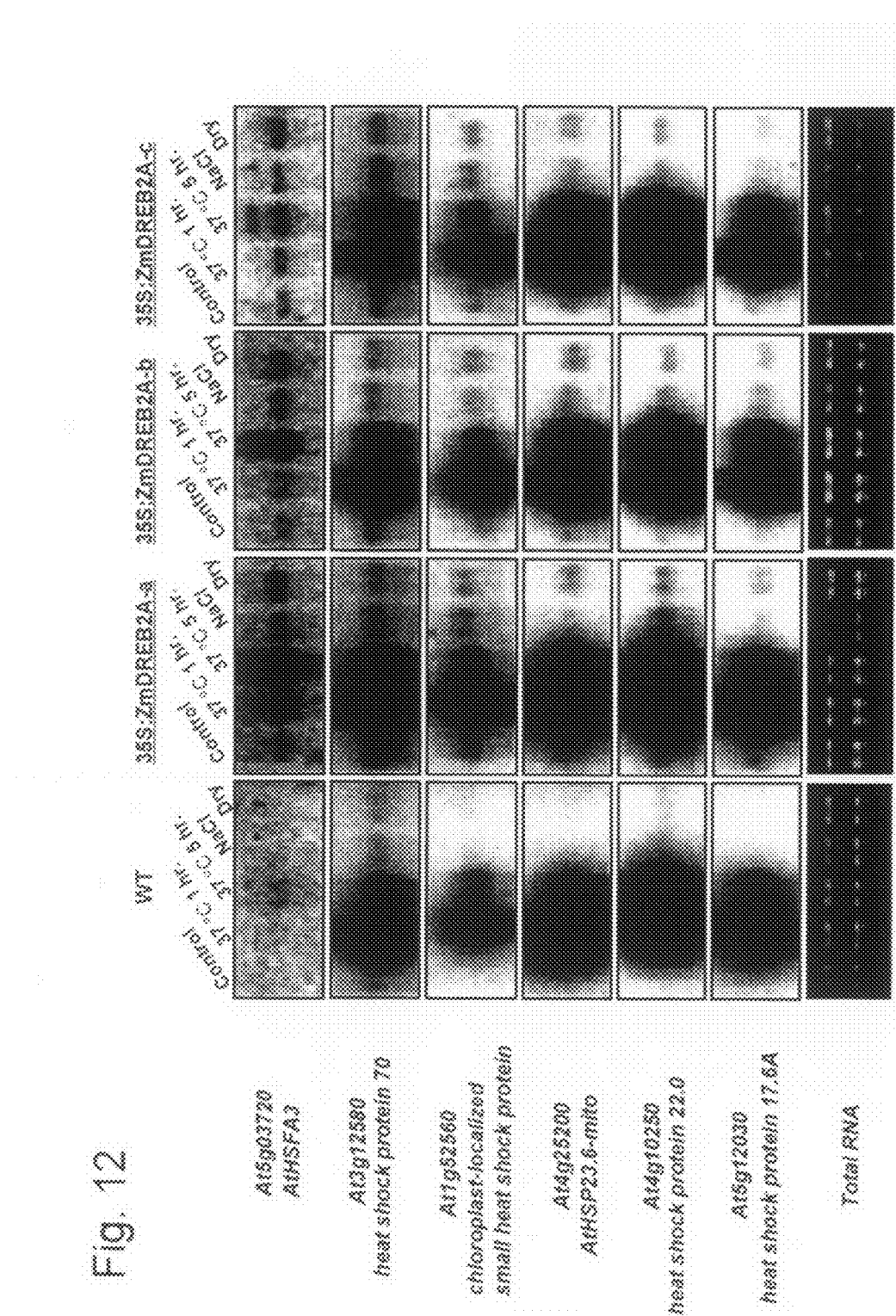
FIG. 12 shows the results of Northern analysis of plants that have been grown under common growth conditions, under high-temperature stress conditions, under salt stress conditions, and under dehydration stress conditions. In the drawing, WT indicates a control plant into which ZmDREB2A has not been introduced; 35S: ZmDREB2A-a, 35S: ZmDREB2A-b, and 35S: ZmDREB2A-c each indicate a plant into which ZmDREB2A has been introduced (3 lines).

The results are shown in FIG. 12. The expression levels of the aforementioned genes were found to be significantly higher in plants into which ZmDREB2A had been introduced than those of a control plant (wild type).

Example 7

Analysis of ZmDREB2A Functions Using Transformant (4)

In accordance with the procedures of Examples 3 and 4, ZmDREB2A was ligated to the rd29A promoter, i.e., a stress inducible promoter, to prepare transgenic *Arabidopsis thaliana* plants (3 lines), and dehydration and low-temperature stress tolerance thereof was analyzed. As a control, *Arabidopsis thaliana* into which ZmDREB2A had not been introduced (i.e., wild type) was allowed to grow in the same manner.

Figure 13:
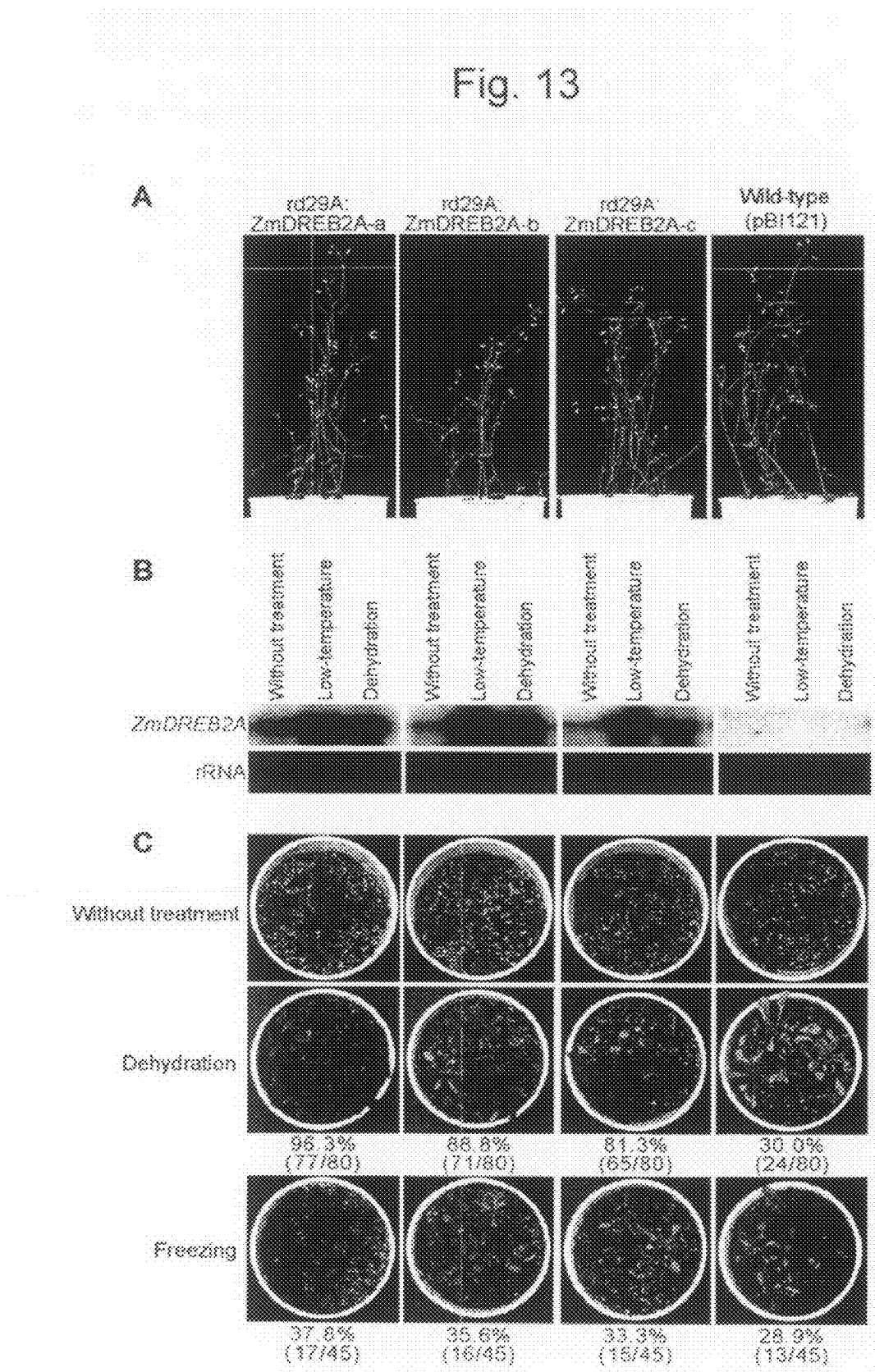
FIG. 13 shows the stress tolerance of ZmDREB2A-overexpressing *Arabidopsis thaliana* using the stress-inducible rd29A promoter. In the drawing, rd29A: ZmDREB2A-a, rd29A: ZmDREB2A-b, and rd29A: ZmDREB2A-c each indicate a plant into which ZmDREB2A has been introduced (3 lines).

The results are shown in FIG. 13. In *Arabidopsis thaliana* plants in which ZmDREB2A is constantly overexpressed with the aid of a 35S promoter, strong growth inhibition was observed (FIG. 8A). In plants in which the expression level of ZmDREB2A is high under the control of the rd29A promoter, however, no obvious retardation of growth was observed, compared with a wild-type plant (FIG. 13A). The accumulation of rd29A mRNA, the expression of which is induced by ZmDREB2A, was increased upon stress application (FIG. 13B). As a result of dehydration stress application by termination of watering for 10 days, only 30% of wild-type *Arabidopsis thaliana* plants survived; however, the three rd29A: ZmDREB2A plants exhibited viabilities of 96.3%, 88.8%, and 81.3%, respectively (FIG. 13C). By regulating expression of ZmDREB2A by the rd29A promoter, dehydration stress tolerance was improved while avoiding growth inhibition. In contrast, improvement in freezing stress tolerance was not as significant as that in dehydration stress tolerance (FIG. 13C), as with the case involving the use of the 35S promoter (FIG. 9A).

Reference Example

High-Temperature Stress Tolerance of Altered (Modified) DREB2A-Overexpressing *Arabidopsis thaliana*

High-temperature stress tolerance of an active DREB2A-overexpressing *Arabidopsis thaliana* plant (DREB2A CA OX) from which a region comprising amino acids 136 to 165 had been deleted was compared with that of a control plant. As a control, an *Arabidopsis thaliana* plant comprising an expression vector without a DREB2A sequence introduced therein was used. Plants that had been grown on GM agar medium for 5 days after sowing were transferred to a filter paper moistened with GM medium, and the plants were allowed to grow for an additional 2 days. The plants 7 days after sowing were subjected to a high-temperature stress tolerance test. High-temperature stress was applied at 22° C., 42° C., 43° C., 44° C., or 45° C. for 1 hour. After high-temperature stress application, the temperature was immediately returned to room temperature, the plants were allowed to grow at that temperature for 1 week, and the viabilities were then determined.

Figure 14:
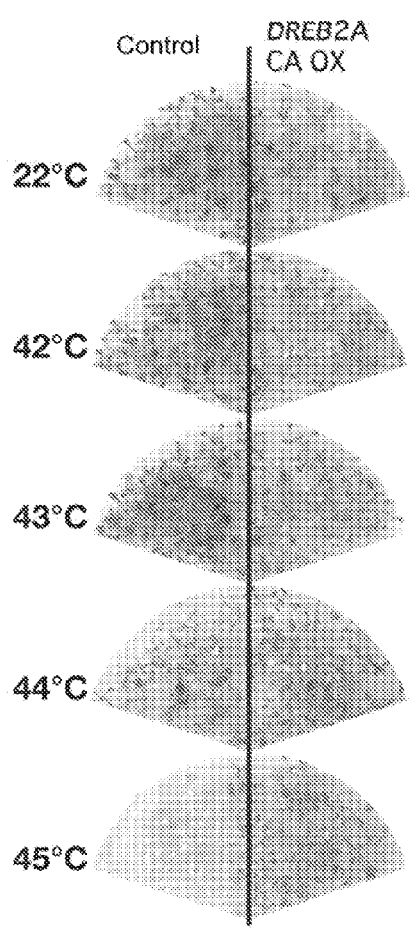
FIG. 14 shows the high-temperature stress tolerance of active DREB2A (modified DREB2A)-overexpressing *Arabidopsis thaliana* using the 35S promoter.

When treated at 42° C. or 43° C., no difference was observed between a control plant and DREB2A CA OX (FIG. 14). However, the viability of a control plant was decreased to 76% when treated at 44° C., and the viability at 45° C. was as low as 2%. In contrast, the viability of DREB2A CA OX was not decreased when treated at 45° C. (FIG. 14).

According to this experiment, ZmDREB2A was found to function in response to environmental stress such as dehydration or high-temperature stress. Further, this experiment suggested the possibility of development of dehydration- and high-temperature stress tolerant crops using the ZmDREB2A gene.

All publications, patents, and patent applications cited herein are incorporated herein by reference in their entirety.

INDUSTRIAL APPLICABILITY

Use of the ZmDREB2A gene according to the present invention can impart plants tolerance to environmental stress, such as dehydration or high-temperature stress, without special modifications. The present invention is accordingly highly useful in preparation of a novel environmental stress tolerant plant.

Free Text of Sequence Listing
SEQ ID NO: 1: cDNA (short-form) of the ZmDREB2A gene
SEQ ID NO: 3: cDNA (long-form) of the ZmDREB2A gene
SEQ ID NOs: 5 to 45: description of artificial sequences: synthetic DNAs (primers)

The invention claimed is:

1. A isolated nucleic acid comprising:
   DNA consisting of the nucleotide sequence as shown in SEQ ID NO: 1.
2. An isolated nucleic acid encoding
   a protein consisting of the amino acid sequence as shown in SEQ ID NO: 2.
3. A recombinant protein comprising:
   a protein consisting of the amino acid sequence as shown in SEQ ID NO: 2.
4. A recombinant vector comprising the isolated nucleic acid according to claim 1 ligated to a stress inducible promoter.
5. The recombinant vector according to claim 4, wherein the stress inducible promoter is a rd29A gene promoter.
6. A host cell transformed with the recombinant vector according to claim 4.
7. The host cell according to claim 6, wherein the stress inducible promoter is a rd29A gene promoter.
8. The transgenic plant transformed with the recombinant vector according to claim 4 and having dehydration and high temperature stress tolerance improved from that of a wild type plant.
9. The transgenic plant according to claim 8, wherein the stress inducible promoter is a rd29A gene promoter.
10. A method of improving stress tolerance of a plant by introducing the recombinant vector according to claim 4 into the plant.
11. The method according to claim 10, wherein the stress inducible promoter is a rd29A gene promoter.

* * * * *